United States Patent
Ho et al.

(10) Patent No.: US 10,633,663 B2
(45) Date of Patent: Apr. 28, 2020

(54) THERAPEUTIC STRATEGIES FOR OVARIAN CANCER: AMHR2-RNA APTAMER

(71) Applicant: University of Cincinnati, Cincinnati, OH (US)

(72) Inventors: Shuk-mei Ho, Cincinnati, OH (US); Pheruza Tarapore, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 82 days.

(21) Appl. No.: 16/119,258

(22) Filed: Aug. 31, 2018

(65) Prior Publication Data

US 2019/0071674 A1 Mar. 7, 2019

Related U.S. Application Data

(60) Provisional application No. 62/553,429, filed on Sep. 1, 2017.

(51) Int. Cl.
*C12N 15/115* (2010.01)
*A61P 35/00* (2006.01)

(52) U.S. Cl.
CPC ............ *C12N 15/115* (2013.01); *A61P 35/00* (2018.01); *C12N 2310/141* (2013.01); *C12N 2310/16* (2013.01); *C12N 2310/322* (2013.01); *C12N 2310/351* (2013.01); *C12N 2310/3519* (2013.01); *C12N 2320/32* (2013.01)

(58) Field of Classification Search
CPC .......................... C12N 15/115; C12N 2310/16
See application file for complete search history.

(56) References Cited

PUBLICATIONS

Shawn E. Lupold, "Aptamers and apple pies: a mini-review of PSMA aptamers and lessons from Donald S. Coffey"; Am J Clin Exp Urol 2018; 6(2): 78-86.
Prince (PSMA-lutetium Radionuclide Therapy and Immunotherapy in Prostate Cancer (Prince); U.S. National Library of Medicine ClinicalTrials.gov, NCT03658447, pp. 1-9, Sep. 2018.
William M. Rockey et al, "Synthesis and radiolabeling of chelator-RNA aptamer bioconjugates with copper-64 for targeted molecular imaging"; Bioorg Med Chem Jul. 1, 2011; 19(13): 4080-4090.

*Primary Examiner* — Brian Whiteman
(74) *Attorney, Agent, or Firm* — Dinsmore & Shohl LLP

(57) ABSTRACT

Various aspects of the invention relate to aptamers that specifically bind Müllerian inhibitory substance II receptor (MISIIR).

19 Claims, 11 Drawing Sheets

Specification includes a Sequence Listing.

SEQUENCE LISTING

```
<160> NUMBER OF SEQ ID NOS: 77

<210> SEQ ID NO 1
<211> LENGTH: 71
<212> TYPE: RNA
<213> ORGANISM: Artificial Sequence
<220> FEATURE:
<223> OTHER INFORMATION: Synthetic

<400> SEQUENCE: 1
gggaggacga ugcggcgcga aagccgauug gugugucguc uauuaucgug ucgggcagac     60
gacucgcccg a                                                         71

<210> SEQ ID NO 2
<211> LENGTH: 12
<212> TYPE: RNA
<213> ORGANISM: Artificial Sequence
<220> FEATURE:
<223> OTHER INFORMATION: Synthetic

<400> SEQUENCE: 2
ggacgaugcg gc                                                        12

<210> SEQ ID NO 3
<211> LENGTH: 12
<212> TYPE: RNA
<213> ORGANISM: Artificial Sequence
<220> FEATURE:
<223> OTHER INFORMATION: Synthetic

<400> SEQUENCE: 3
ggugugucgu cu                                                        12

<210> SEQ ID NO 4
<211> LENGTH: 35
<212> TYPE: RNA
<213> ORGANISM: Artificial Sequence
<220> FEATURE:
<223> OTHER INFORMATION: Synthetic

<400> SEQUENCE: 4
cgcgaaagcc gauuggugug ucgucuauua ucgug                               35

<210> SEQ ID NO 5
<211> LENGTH: 71
<212> TYPE: RNA
```

```
<213> ORGANISM: Artificial Sequence
<220> FEATURE:
<223> OTHER INFORMATION: Synthetic

<400> SEQUENCE: 5
gggaggacga ugcgggaagc acgucccgag guauauguuu cguagucgcu gugggcagac    60
gacucgcccg a                                                        71

<210> SEQ ID NO 6
<211> LENGTH: 35
<212> TYPE: RNA
<213> ORGANISM: Artificial Sequence
<220> FEATURE:
<223> OTHER INFORMATION: Synthetic

<400> SEQUENCE: 6
gaagcacguc ccgagguaua uguuucguag ucgcu                               35

<210> SEQ ID NO 7
<211> LENGTH: 71
<212> TYPE: RNA
<213> ORGANISM: Artificial Sequence
<220> FEATURE:
<223> OTHER INFORMATION: Synthetic

<400> SEQUENCE: 7
gggaggacga ugcggccaua ccgugaagcc uuggcugcau cgggauuuug gucggcagac    60
gacucgcccg a                                                        71

<210> SEQ ID NO 8
<211> LENGTH: 35
<212> TYPE: RNA
<213> ORGANISM: Artificial Sequence
<220> FEATURE:
<223> OTHER INFORMATION: Synthetic

<400> SEQUENCE: 8
ccauaccgug aagccuuggc ugcaucggga uuuug                               35

<210> SEQ ID NO 9
<211> LENGTH: 88
<212> TYPE: RNA
<213> ORGANISM: Artificial Sequence
<220> FEATURE:
<223> OTHER INFORMATION: Synthetic

<400> SEQUENCE: 9
uaauacgacu cacuauaggg aggacgaugc ggcacaaucg dacuauguuu cuccgguugc    60
ccgccugcug ugcagacgac ucgcccga                                      88

<210> SEQ ID NO 10
<211> LENGTH: 88
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: n is a, c, g, or u

<400> SEQUENCE: 10
uaauacgacu cacuauaggg aggnggaugg ggcacaaucg gacuauguuu cuccgguugc    60
ccgccugcug ugcagacgac ucgcccga                                      88
```

```
<210> SEQ ID NO 11
<211> LENGTH: 88
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or u

<400> SEQUENCE: 11
uaauacgacu cacuauaggg nggacgaugc ggccgauaac gcggugaaug uuugcggucc      60
ucucgcgugu gccagacgac ucgcccga                                        88

<210> SEQ ID NO 12
<211> LENGTH: 87
<212> TYPE: RNA
<213> ORGANISM: Artificial Sequence
<220> FEATURE:
<223> OTHER INFORMATION: Synthetic

<400> SEQUENCE: 12
uaauacgacu cacuauaggg aggacgaugc gguaccuccg ccuaucguua uaaggauguu      60
cucgcguugg ccagacgacu cgcccga                                         87

<210> SEQ ID NO 13
<211> LENGTH: 88
<212> TYPE: RNA
<213> ORGANISM: Artificial Sequence
<220> FEATURE:
<223> OTHER INFORMATION: Synthetic

<400> SEQUENCE: 13
uaauacgacu cacuauaggg aggacgaugc ggccuguguu ucgccgcauc cauagucuau      60
cguuugugug ugcagacgac ucgcccga                                        88

<210> SEQ ID NO 14
<211> LENGTH: 88
<212> TYPE: RNA
<213> ORGANISM: Artificial Sequence
<220> FEATURE:
<223> OTHER INFORMATION: Synthetic

<400> SEQUENCE: 14
uaauacgacu cacuauaggg aggacgaugc ggcgcaaaag ccgauuggug ugcgucuau       60 uaucgugucg ugcagacgac ucgcccga                                        88

<210> SEQ ID NO 15
<211> LENGTH: 88
<212> TYPE: RNA
<213> ORGANISM: Artificial Sequence
<220> FEATURE:
<223> OTHER INFORMATION: Synthetic

<400> SEQUENCE: 15
uaauacgacu cacuauaggg aggacgaugc ggcgcaaaag ccgauuggug ugcgucuau       60 uaucgugucg ugcagacgac ucgcccga                                        88

<210> SEQ ID NO 16
<211> LENGTH: 88
<212> TYPE: RNA
```

<213> ORGANISM: Artificial Sequence
<220> FEATURE:
<223> OTHER INFORMATION: Synthetic

<400> SEQUENCE: 16
uaauacgacu cacuauaggg aggacgaugc ggcgcaaaag ccgauuggug ugucgucuau    60
uaucgugucg ugcagacgac ucgcccga                                      88

<210> SEQ ID NO 17
<211> LENGTH: 88
<212> TYPE: RNA
<213> ORGANISM: Artificial Sequence
<220> FEATURE:
<223> OTHER INFORMATION: Synthetic

<400> SEQUENCE: 17
uaauacgacu cacuauaggg aggacgaugc ggcgcaaaag ccgauuggug ugucgucuau    60
uaucgugucg ugcagacgac ucgcccga                                      88

<210> SEQ ID NO 18
<211> LENGTH: 88
<212> TYPE: RNA
<213> ORGANISM: Artificial Sequence
<220> FEATURE:
<223> OTHER INFORMATION: Synthetic

<400> SEQUENCE: 18
uaauacgacu cacuauaggg aggacgaugc ggcgcaaaag ccgauuggug ugucgucuau    60
uaucgugucg ugcagacgac ucgcccga                                      88

<210> SEQ ID NO 19
<211> LENGTH: 88
<212> TYPE: RNA
<213> ORGANISM: Artificial Sequence
<220> FEATURE:
<223> OTHER INFORMATION: Synthetic

<400> SEQUENCE: 19
uaauacgacu cacuauaggg aggacgaugc ggcgcaaaag ccgauuggug ugucguccau    60
uaucgugucg ugcagacgac ucgcccga                                      88

<210> SEQ ID NO 20
<211> LENGTH: 88
<212> TYPE: RNA
<213> ORGANISM: Artificial Sequence
<220> FEATURE:
<223> OTHER INFORMATION: Synthetic

<400> SEQUENCE: 20
uaauacgacu cacuauaggg aggacgaugc ggcgcgaaag ccgauuggug ugucguccau    60
uaucgugucg ugcagacgac ucgcccga                                      88

<210> SEQ ID NO 21
<211> LENGTH: 88
<212> TYPE: RNA
<213> ORGANISM: Artificial Sequence
<220> FEATURE:
<223> OTHER INFORMATION: Synthetic

<400> SEQUENCE: 21
uaauacgacu cacuauaggg aggacgaugc ggcgcgaaag ccgauuggug ugucguccau    60
uaucgugucg ugcagacgac ucgcccga                                      88

```
<210> SEQ ID NO 22
<211> LENGTH: 88
<212> TYPE: RNA
<213> ORGANISM: Artificial Sequence
<220> FEATURE:
<223> OTHER INFORMATION: Synthetic

<400> SEQUENCE: 22
uaauacgacu cacuauaggg aggacgaugc ggcgcgaaag ccgauuggug ugucguccau      60
uaucgugucg ugcagacgac ucgcccga                                        88

<210> SEQ ID NO 23
<211> LENGTH: 88
<212> TYPE: RNA
<213> ORGANISM: Artificial Sequence
<220> FEATURE:
<223> OTHER INFORMATION: Synthetic

<400> SEQUENCE: 23
uaauacgacu cacuauaggg aggacgaugc ggcgcgaaag ccgauugguz ugucguccau      60 aaucgugucg ugcagacgac ucgcccga                                        88

<210> SEQ ID NO 24
<211> LENGTH: 88
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a, c, g, or u

<400> SEQUENCE: 24
uaauacnacu cacuauaggg aggacgaugc ggcgcgaaag ccgauuggcg ugucguccau      60
uaucgugucc ugcagacgac ucgcccga                                        88

<210> SEQ ID NO 25
<211> LENGTH: 89
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (14)..(14)
<223> OTHER INFORMATION: n is a, c, g, or u
<220> FEATURE:
<221> NAME/KEY: misc_feature
<222> LOCATION: (43)..(45)
<223> OTHER INFORMATION: n is a, c, g, or u
<220> FEATURE:
<221> NAME/KEY: misc_feature
<222> LOCATION: (50)..(50)
<223> OTHER INFORMATION: n is a, c, g, or u

<400> SEQUENCE: 25
nnnguacgac ucanauaugg gaggacgaug cggcgcgaaa gunnnuuggn gugucgucca      60
uuaucguguc gugcagacga cucgcccga                                       89

<210> SEQ ID NO 26
```

```
<211> LENGTH: 88
<212> TYPE: RNA
<213> ORGANISM: Artificial Sequence
<220> FEATURE:
<223> OTHER INFORMATION: Synthetic

<400> SEQUENCE: 26
uaauacgacu cacuauaggg aggacgaugc ggcgcgaaag ccgauuggug ugucgucaau    60
uaucgugucg ugcagacgac ucgcccga                                      88

<210> SEQ ID NO 27
<211> LENGTH: 87
<212> TYPE: RNA
<213> ORGANISM: Artificial Sequence
<220> FEATURE:
<223> OTHER INFORMATION: Synthetic

<400> SEQUENCE: 27
uauacgacuc acuauaggga ggacgaugcg gcgcgaaagc cgauuggugu gucgucuauu    60
aucgugucgu gcagacgacu cgcccga                                       87

<210> SEQ ID NO 28
<211> LENGTH: 90
<212> TYPE: RNA
<213> ORGANISM: Artificial Sequence
<220> FEATURE:
<223> OTHER INFORMATION: Synthetic

<400> SEQUENCE: 28
aauacgacuc acuauaggga ggacgaugcg gcgcgaaagc cgauuggugu gucgucuauu    60
aucgugucgu gcagacgacu cgcccgaagc                                    90

<210> SEQ ID NO 29
<211> LENGTH: 88
<212> TYPE: RNA
<213> ORGANISM: Artificial Sequence
<220> FEATURE:
<223> OTHER INFORMATION: Synthetic

<400> SEQUENCE: 29
uaauacgacu cacuauaggg aggacgaugc ggcggaaagc cgauuggugu gucgucuauu    60
aucgugucgu gcagacgacu cgcccgaa                                      88

<210> SEQ ID NO 30
<211> LENGTH: 89
<212> TYPE: RNA
<213> ORGANISM: Artificial Sequence
<220> FEATURE:
<223> OTHER INFORMATION: Synthetic

<400> SEQUENCE: 30
uaauacgacu cacuauaggg aggacgaugc ggcgcgaaag ccgauuggug ugucgucuau    60
uaucgugucg ugcagacgac ucgcccgaa                                     89

<210> SEQ ID NO 31
<211> LENGTH: 88
<212> TYPE: RNA
<213> ORGANISM: Artificial Sequence
<220> FEATURE:
<223> OTHER INFORMATION: Synthetic

<400> SEQUENCE: 31
uaauacgacu cacuauaggg aggacgaugc ggcgagaaag ccgauuggug ugucgucuau    60
```
uaucgugucg ugcagacgac ucgcccga                                              88

<210> SEQ ID NO 32
<211> LENGTH: 88
<212> TYPE: RNA
<213> ORGANISM: Artificial Sequence
<220> FEATURE:
<223> OTHER INFORMATION: Synthetic

<400> SEQUENCE: 32
uaauacgacu cacuauaggg aggacgaugc ggcgggaaag ccgauuggug ugucgucuau        60
uaucgugucg ugcagacgac ucgcccga                                              88

<210> SEQ ID NO 33
<211> LENGTH: 88
<212> TYPE: RNA
<213> ORGANISM: Artificial Sequence
<220> FEATURE:
<223> OTHER INFORMATION: Synthetic

<400> SEQUENCE: 33
uaauacgacu cacuauaggg aggacgaugc ggcgcgaaag ccgauuggug ugucgucuau        60
uaucgugucg ugcagacgac ucgcccga                                              88

<210> SEQ ID NO 34
<211> LENGTH: 88
<212> TYPE: RNA
<213> ORGANISM: Artificial Sequence
<220> FEATURE:
<223> OTHER INFORMATION: Synthetic

<400> SEQUENCE: 34
uaauacgacu cacuauaggg aggacgaugc ggcgcgaaag ccgauuggug ugucgucuau        60
uaucgugucg ugcagacgac ucgcccga                                              88

<210> SEQ ID NO 35
<211> LENGTH: 88
<212> TYPE: RNA
<213> ORGANISM: Artificial Sequence
<220> FEATURE:
<223> OTHER INFORMATION: Synthetic

<400> SEQUENCE: 35
uaauacgacu cacuauaggg aggacgaugc ggcgcgaaag ccgauuggug ugucgucuau        60
uaucgugucg ugcagacgac ucgcccga                                              88

<210> SEQ ID NO 36
<211> LENGTH: 88
<212> TYPE: RNA
<213> ORGANISM: Artificial Sequence
<220> FEATURE:
<223> OTHER INFORMATION: Synthetic

<400> SEQUENCE: 36
uaauacgacu cacuauaggg aggacgaugc ggcgcgaaag ccgauuggug ugucgucuau        60
uaucgugucg ugcagacgac ucgcccga                                              88

<210> SEQ ID NO 37
<211> LENGTH: 89
<212> TYPE: RNA
<213> ORGANISM: Artificial Sequence
<220> FEATURE:

<223> OTHER INFORMATION: Synthetic

<400> SEQUENCE: 37
uaauacgacu cacuauaggg aggacgaugc ggcgcgaaag ccgauuggug ugucgucuau    60
uaucgugucg ugcagacgac ucgcccgaa    89

<210> SEQ ID NO 38
<211> LENGTH: 88
<212> TYPE: RNA
<213> ORGANISM: Artificial Sequence
<220> FEATURE:
<223> OTHER INFORMATION: Synthetic

<400> SEQUENCE: 38
uaauacgacu cacuauaggg aggacgaugc ggcgcgaaag ccgauuggug ugucgucuau    60
uaucgugucg ugcagacgac ucgcccga    88

<210> SEQ ID NO 39
<211> LENGTH: 88
<212> TYPE: RNA
<213> ORGANISM: Artificial Sequence
<220> FEATURE:
<223> OTHER INFORMATION: Synthetic

<400> SEQUENCE: 39
uaauacgacu cacuauaggg aggacgaugc ggcgcgaaag ccgauuggug ugucgucuau    60
uaucgugucg ugcagacgac ucgcccga    88

<210> SEQ ID NO 40
<211> LENGTH: 88
<212> TYPE: RNA
<213> ORGANISM: Artificial Sequence
<220> FEATURE:
<223> OTHER INFORMATION: Synthetic

<400> SEQUENCE: 40
uaauacgacu cacuauaggg aggacgaugc ggcgcgaaag ccgauuggug ugucgucuau    60
uaucgugucg ugcagacgac ucgcccga    88

<210> SEQ ID NO 41
<211> LENGTH: 88
<212> TYPE: RNA
<213> ORGANISM: Artificial Sequence
<220> FEATURE:
<223> OTHER INFORMATION: Synthetic

<400> SEQUENCE: 41
uaauacgacu cacuauaggg aggacgaugc ggcgcgaaag ccgauuggug ugucgucuau    60
uaucgugucg ugcagacgac ucgcccga    88

<210> SEQ ID NO 42
<211> LENGTH: 88
<212> TYPE: RNA
<213> ORGANISM: Artificial Sequence
<220> FEATURE:
<223> OTHER INFORMATION: Synthetic

<400> SEQUENCE: 42
uaauacgacu cacuauaggg aggacgaugc ggcgcgaaag ccgauuggug ugucgucuau    60
uaucgugucg ugcagacgac ucgcccga    88

```
<210> SEQ ID NO 43
<211> LENGTH: 88
<212> TYPE: RNA
<213> ORGANISM: Artificial Sequence
<220> FEATURE:
<223> OTHER INFORMATION: Synthetic

<400> SEQUENCE: 43
uaauacgacu cacuauaggg aggacgaugc ggcgcgaaag ccgauuggug ugucgucuau    60
uaucgugucg ugcagacgac ucgcccga                                       88

<210> SEQ ID NO 44
<211> LENGTH: 88
<212> TYPE: RNA
<213> ORGANISM: Artificial Sequence
<220> FEATURE:
<223> OTHER INFORMATION: Synthetic

<400> SEQUENCE: 44
uaauacgacu cacuauaggg aggacgaugc ggcgcgaaag ccgauuggug ugucgucuau    60
uaucgugucg ugcagacgac ucgcccga                                       88

<210> SEQ ID NO 45
<211> LENGTH: 88
<212> TYPE: RNA
<213> ORGANISM: Artificial Sequence
<220> FEATURE:
<223> OTHER INFORMATION: Synthetic

<400> SEQUENCE: 45
uaauacgacu cacuauaggg aggacgaugc ggcgcgaaag ccgauuggug ugucgucuau    60
uaucgugucg ugcagacgac ucgcccga                                       88

<210> SEQ ID NO 46
<211> LENGTH: 80
<212> TYPE: RNA
<213> ORGANISM: Artificial Sequence
<220> FEATURE:
<223> OTHER INFORMATION: Synthetic

<400> SEQUENCE: 46
uaauacgacu cacuauaggg aggacgaugc ggcgcgaaag ccgauuggug ugucgucuau    60
uaucgugucg ugcagacgac                                                80

<210> SEQ ID NO 47
<211> LENGTH: 88
<212> TYPE: RNA
<213> ORGANISM: Artificial Sequence
<220> FEATURE:
<223> OTHER INFORMATION: Synthetic

<400> SEQUENCE: 47
uaauacgacu cacuauaggg aggacgaugc ggcgcgaaag ccgauuggug ugucgucuau    60
uaucgugucg ugcagacgac ucgcccga                                       88

<210> SEQ ID NO 48
<211> LENGTH: 88
<212> TYPE: RNA
<213> ORGANISM: Artificial Sequence
<220> FEATURE:
<223> OTHER INFORMATION: Synthetic

<400> SEQUENCE: 48
```
uaauacgacu cacuauaggg aggacgaugc ggcgcgaaag ccgauuggug ugucgucuau     60
uaucgugucg ugcagacgac ucgcccga                                        88

<210> SEQ ID NO 49
<211> LENGTH: 88
<212> TYPE: RNA
<213> ORGANISM: Artificial Sequence
<220> FEATURE:
<223> OTHER INFORMATION: Synthetic

<400> SEQUENCE: 49
uaauacgacu cacuauaggg aggacgaugc ggcgcgaaag ccgauuggug ugucgucuau     60
uaucgugucg ugcagacgac ucgcccga                                        88

<210> SEQ ID NO 50
<211> LENGTH: 88
<212> TYPE: RNA
<213> ORGANISM: Artificial Sequence
<220> FEATURE:
<223> OTHER INFORMATION: Synthetic

<400> SEQUENCE: 50
uaauacgacu cacuauaggg aggacgaugc ggcgcgaaag ccgauuggug ugucgucuau     60
uaucgugucg ugcagacgac ucgcccga                                        88

<210> SEQ ID NO 51
<211> LENGTH: 88
<212> TYPE: RNA
<213> ORGANISM: Artificial Sequence
<220> FEATURE:
<223> OTHER INFORMATION: Synthetic

<400> SEQUENCE: 51
uaauacgacu cacuauaggg aggacgaugc ggcgcgaaag ccgauuggug ugucgucuau     60
uaucgugucg ugcagacgac ucgcccga                                        88

<210> SEQ ID NO 52
<211> LENGTH: 88
<212> TYPE: RNA
<213> ORGANISM: Artificial Sequence
<220> FEATURE:
<223> OTHER INFORMATION: Synthetic

<400> SEQUENCE: 52
uaauacgacu cacuauaggg aggacgaugc ggcgcgaaag ccgauuggug ugucgucuau     60
uaucgugucg ugcagacgac ucgcccga                                        88

<210> SEQ ID NO 53
<211> LENGTH: 88
<212> TYPE: RNA
<213> ORGANISM: Artificial Sequence
<220> FEATURE:
<223> OTHER INFORMATION: Synthetic

<400> SEQUENCE: 53
uaauacgacu cacuauaggg aggacgaugc gggaagcacg ucccgaggua uauguuucgu     60
agucgcugug ggcagacgac ucgcccga                                        88

<210> SEQ ID NO 54
<211> LENGTH: 88
<212> TYPE: RNA
<213> ORGANISM: Artificial Sequence

```
<220> FEATURE:
<223> OTHER INFORMATION: Synthetic

<400> SEQUENCE: 54
uaauacgacu cacuauaggg aggacgaugc gggaagcacg ucccgaggua uauguuucgu     60
agucgcugug ggcagacgac ucgcccga                                       88

<210> SEQ ID NO 55
<211> LENGTH: 88
<212> TYPE: RNA
<213> ORGANISM: Artificial Sequence
<220> FEATURE:
<223> OTHER INFORMATION: Synthetic

<400> SEQUENCE: 55
uaauacgacu cacuauaggg aggacgaugc gggaagcacg ucccgaggua uauguuucgu     60
agucgcugug ggcagacgac ucgcccga                                       88

<210> SEQ ID NO 56
<211> LENGTH: 88
<212> TYPE: RNA
<213> ORGANISM: Artificial Sequence
<220> FEATURE:
<223> OTHER INFORMATION: Synthetic

<400> SEQUENCE: 56
uaauacgacu cacuauaggg aggacgaugc gggaagcacg ucccgaggua uauguuucgu     60
agucgcugug ggcagacgac ucgcccga                                       88

<210> SEQ ID NO 57
<211> LENGTH: 88
<212> TYPE: RNA
<213> ORGANISM: Artificial Sequence
<220> FEATURE:
<223> OTHER INFORMATION: Synthetic

<400> SEQUENCE: 57
uaauacgacu cacuauaggg aggacgaugc gggaagcacg ucccgaggua uauguuucgu     60
agucgcugug ggcagacgac ucgcccga                                       88

<210> SEQ ID NO 58
<211> LENGTH: 88
<212> TYPE: RNA
<213> ORGANISM: Artificial Sequence
<220> FEATURE:
<223> OTHER INFORMATION: Synthetic

<400> SEQUENCE: 58
uaauacgacu cacuauaggg aggacgaugc gggaagcacg ucccgaggua uauguuucgu     60
agucgcugug ggcagacgac ucgcccga                                       88

<210> SEQ ID NO 59
<211> LENGTH: 88
<212> TYPE: RNA
<213> ORGANISM: Artificial Sequence
<220> FEATURE:
<223> OTHER INFORMATION: Synthetic

<400> SEQUENCE: 59
uaauacgacu cacuauaggg aggacgaugc gggaagcacg ucccgaggua uauguuucgu     60
agucgcugug ggcagacgac ucgcccga                                       88
```

```
<210> SEQ ID NO 60
<211> LENGTH: 88
<212> TYPE: RNA
<213> ORGANISM: Artificial Sequence
<220> FEATURE:
<223> OTHER INFORMATION: Synthetic

<400> SEQUENCE: 60
uaauacgacu cacuauaggg aggacgaugc gggaagcacg ucccgaggua uauguuucgu    60
agucgcugug ggcagacgac ucgcccga                                      88

<210> SEQ ID NO 61
<211> LENGTH: 88
<212> TYPE: RNA
<213> ORGANISM: Artificial Sequence
<220> FEATURE:
<223> OTHER INFORMATION: Synthetic

<400> SEQUENCE: 61
uaauacgacu cacuauaggg aggacgaugc gggaagcacg ucccgaggua uauguuucgu    60
agucgcugug ggcagacgac ucgcccga                                      88

<210> SEQ ID NO 62
<211> LENGTH: 88
<212> TYPE: RNA
<213> ORGANISM: Artificial Sequence
<220> FEATURE:
<223> OTHER INFORMATION: Synthetic

<400> SEQUENCE: 62
uaauacgacu cacuauaggg aggacgaugc gggaagcacg ucccguggua uauguuucgu    60
agucgcugug ggcagacgac ucgcccga                                      88

<210> SEQ ID NO 63
<211> LENGTH: 88
<212> TYPE: RNA
<213> ORGANISM: Artificial Sequence
<220> FEATURE:
<223> OTHER INFORMATION: Synthetic

<400> SEQUENCE: 63
uaauacgacu cacuauaggg aggacgaugc gggaagcacg ucccuaggua uauguuuggu    60
agucgcuggg ggcagacgac ucgcccga                                      88

<210> SEQ ID NO 64
<211> LENGTH: 87
<212> TYPE: RNA
<213> ORGANISM: Artificial Sequence
<220> FEATURE:
<223> OTHER INFORMATION: Synthetic

<400> SEQUENCE: 64
uaaugcgacu cacuauaggg aggacgaugg gggaagaauu caugagguag auguuuugua    60
gucccggugg ccagaggacu ccccgga                                       87

<210> SEQ ID NO 65
<211> LENGTH: 88
<212> TYPE: RNA
<213> ORGANISM: Artificial Sequence
<220> FEATURE:
<223> OTHER INFORMATION: Synthetic

<400> SEQUENCE: 65
```
uaauacgacu cacuauaggg aggacgaugc gggaagcacg ucccgaggua uauguuucgu    60
agucgcugug ggcagacgac ucgcccga                                       88

<210> SEQ ID NO 66
<211> LENGTH: 88
<212> TYPE: RNA
<213> ORGANISM: Artificial Sequence
<220> FEATURE:
<223> OTHER INFORMATION: Synthetic

<400> SEQUENCE: 66
uaauacgacu cacuauaggg aggacgaugc gggaagcacg ucccgaggua uauguuucgu    60
agucgcugug ggcagacgac ucgcccga                                       88

<210> SEQ ID NO 67
<211> LENGTH: 88
<212> TYPE: RNA
<213> ORGANISM: Artificial Sequence
<220> FEATURE:
<223> OTHER INFORMATION: Synthetic

<400> SEQUENCE: 67
uaauacgacu cacuauaggg aggacgaugc gggaagcacg ucccgaggua uauguuucgu    60
agucgcugug ggcagacgac ucgcccga                                       88

<210> SEQ ID NO 68
<211> LENGTH: 88
<212> TYPE: RNA
<213> ORGANISM: Artificial Sequence
<220> FEATURE:
<223> OTHER INFORMATION: Synthetic

<400> SEQUENCE: 68
uaauacgacu cacuauaggg aggacgaugc gggaagcacg ucccgaggua uauguuucgu    60
agucgcugug ggcagacgac ucgcccga                                       88

<210> SEQ ID NO 69
<211> LENGTH: 88
<212> TYPE: RNA
<213> ORGANISM: Artificial Sequence
<220> FEATURE:
<223> OTHER INFORMATION: Synthetic

<400> SEQUENCE: 69
uaauacgacu cacuauaggg aggacgaugc gggaagcacg ucccgaggua uauguuucgu    60
agucgcugug ggcagacgac ucgcccga                                       88

<210> SEQ ID NO 70
<211> LENGTH: 88
<212> TYPE: RNA
<213> ORGANISM: Artificial Sequence
<220> FEATURE:
<223> OTHER INFORMATION: Synthetic

<400> SEQUENCE: 70
uaauacgacu cacuauaggg aggacgaugc gggaagcacg ucccgaggua uauguuucgu    60
agucgcugug ggcagacgac ucgcccga                                       88

<210> SEQ ID NO 71
<211> LENGTH: 88
<212> TYPE: RNA

```
<213> ORGANISM: Artificial Sequence
<220> FEATURE:
<223> OTHER INFORMATION: Synthetic

<400> SEQUENCE: 71
uaauacgacu cacuauaggg aggacgaugc gggaagcacg ucccgaggua uauguuucgu      60
agucgcugug ggcagacgac ucgcccga                                         88

<210> SEQ ID NO 72
<211> LENGTH: 88
<212> TYPE: RNA
<213> ORGANISM: Artificial Sequence
<220> FEATURE:
<223> OTHER INFORMATION: Synthetic

<400> SEQUENCE: 72
uaauacgacu cacuauaggg aggacgaugc gggaagcacg ucccgaggua uauguuucgu      60
agucgcugug ggcagacgac ucgcccga                                         88

<210> SEQ ID NO 73
<211> LENGTH: 88
<212> TYPE: RNA
<213> ORGANISM: Artificial Sequence
<220> FEATURE:
<223> OTHER INFORMATION: Synthetic

<400> SEQUENCE: 73
uaauacgacu cacuauaggg aggacgaugc gggaagcacg ucccgaggua uauguuucgu      60
agucgcugug ggcagacgac ucgcccga                                         88

<210> SEQ ID NO 74
<211> LENGTH: 88
<212> TYPE: RNA
<213> ORGANISM: Artificial Sequence
<220> FEATURE:
<223> OTHER INFORMATION: Synthetic

<400> SEQUENCE: 74
uaauacgacu cacuauaggg aggacgaugc gggaagcacg ucccguggua uauguuucgu      60
agucgcugug ggcagacgac ucgcccga                                         88

<210> SEQ ID NO 75
<211> LENGTH: 88
<212> TYPE: RNA
<213> ORGANISM: Artificial Sequence
<220> FEATURE:
<223> OTHER INFORMATION: Synthetic

<400> SEQUENCE: 75
uaauacgacu cacuauaggg aggacgaugc gggaagcacg ucccuaggua uauguuuggu      60
agucgcuggg ggcagacgac ucgcccga                                         88

<210> SEQ ID NO 76
<211> LENGTH: 87
<212> TYPE: RNA
<213> ORGANISM: Artificial Sequence
<220> FEATURE:
<223> OTHER INFORMATION: Synthetic

<400> SEQUENCE: 76
uaaugcgacu cacuauaggg aggacgaugg gggaagaauu caugagguag auguuugua       60 gucccggugg ccagaggacu ccccgga                                          87
```

```
<210> SEQ ID NO 77
<211> LENGTH: 88
<212> TYPE: RNA
<213> ORGANISM: Artificial Sequence
<220> FEATURE:
<223> OTHER INFORMATION: Synthetic

<400> SEQUENCE: 77
uaauacgacu cacuauaggg aggacgaugc ggcguguacg agcccaauag ggauguuaga      60
cuacacgcgg ggcagacgac ucgcccga                                         88
```

US 10,633,663 B2

THERAPEUTIC STRATEGIES FOR OVARIAN CANCER: AMHR2-RNA APTAMER

PRIORITY CLAIM

This application claims priority under 35 U.S.C. § 119(e) to U.S. Provisional Patent Application No. 62/553,429, filed Sep. 1, 2017, which is hereby incorporated by reference in its entirety.

BACKGROUND

Ovarian cancer is the second most common gynecological cancer and causes more deaths than any other cancer of the female reproductive tract. The annual incidence of ovarian cancer is about 12.3 individuals per 100,000 individuals per year, and the 5-year survival rate for individuals diagnosed with ovarian cancer is 46.5%. Malignant epithelial ovarian carcinoma is most prevalent. Treatment options include surgery followed by intraperitoneal or systemic chemotherapy such as platinum-based therapies, alkylating agents, and/or taxenes. Chemotherapy-associated toxicity often results in side effects that detrimentally affect quality of life. Improved methods of treating ovarian cancer are therefore desirable.

SUMMARY

Accordingly, embodiments of the invention provide compositions and methods that allow for the improved treatment of ovarian cancer. The disclosed compositions and methods allow precise targeting of carcinogenic cells, including metastasized cells, which mitigates the toxic side effects of traditional chemotherapeutic agents.

One embodiment is directed to an aptamer, comprising a nucleotide sequence having at least 95% sequence homology with at least 24 consecutive nucleotides of the nucleotide sequence set forth in SEQ ID NO:4.

Another embodiment is directed to an aptamer, comprising a nucleotide sequence having at least 95% sequence homology with at least 24 consecutive nucleotides of the nucleotide sequence set forth in any one of SEQ ID NO:9 to SEQ ID NO:76.

Another embodiment is directed to a method of treating a human subject, comprising administering an aptamer to the subject, wherein the aptamer comprises a nucleotide sequence having at least 95% sequence homology with at least 24 consecutive nucleotides of the nucleotide sequence set forth in SEQ ID NO:4.

These and other aspects and embodiments will be detailed and clarified by reference to the Drawings and Detailed Description, below.

BRIEF DESCRIPTION OF THE DRAWINGS

Figures have been provided to illustrate specific embodiments, aspects, and features of the invention and should not be construed as limiting the full scope thereof as defined by the appended claims.

DETAILED DESCRIPTION

Figure 1:
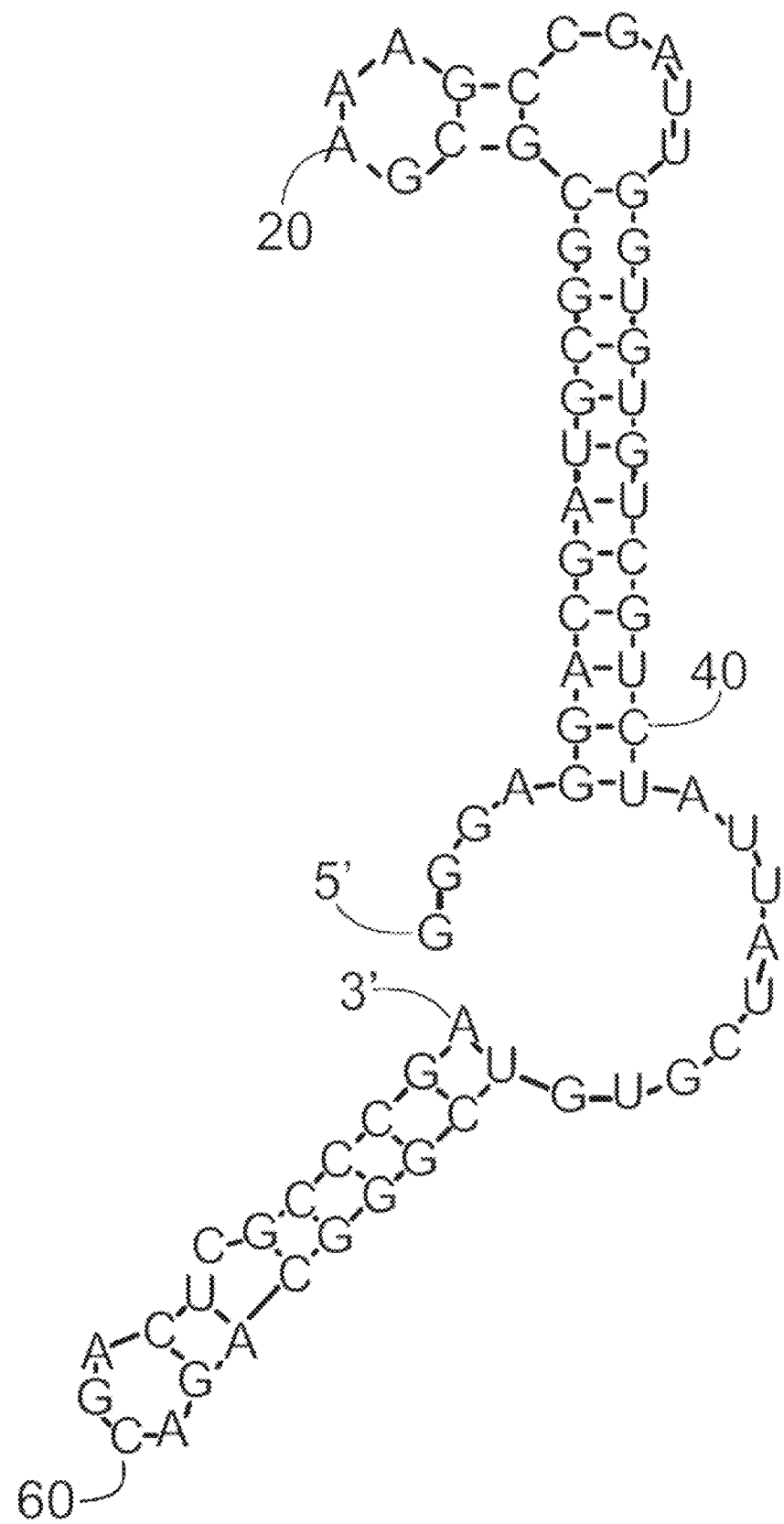
FIG. 1 is a representation of the secondary structure of Compound I as depicted with the nucleotide sequence set forth in SEQ ID NO:1. Other nucleotide sequences may have the 2-dimensional structure of Compound I including 2'-fluoropyrimidine-substituted variants of SEQ ID NO:1.
Figure 2:
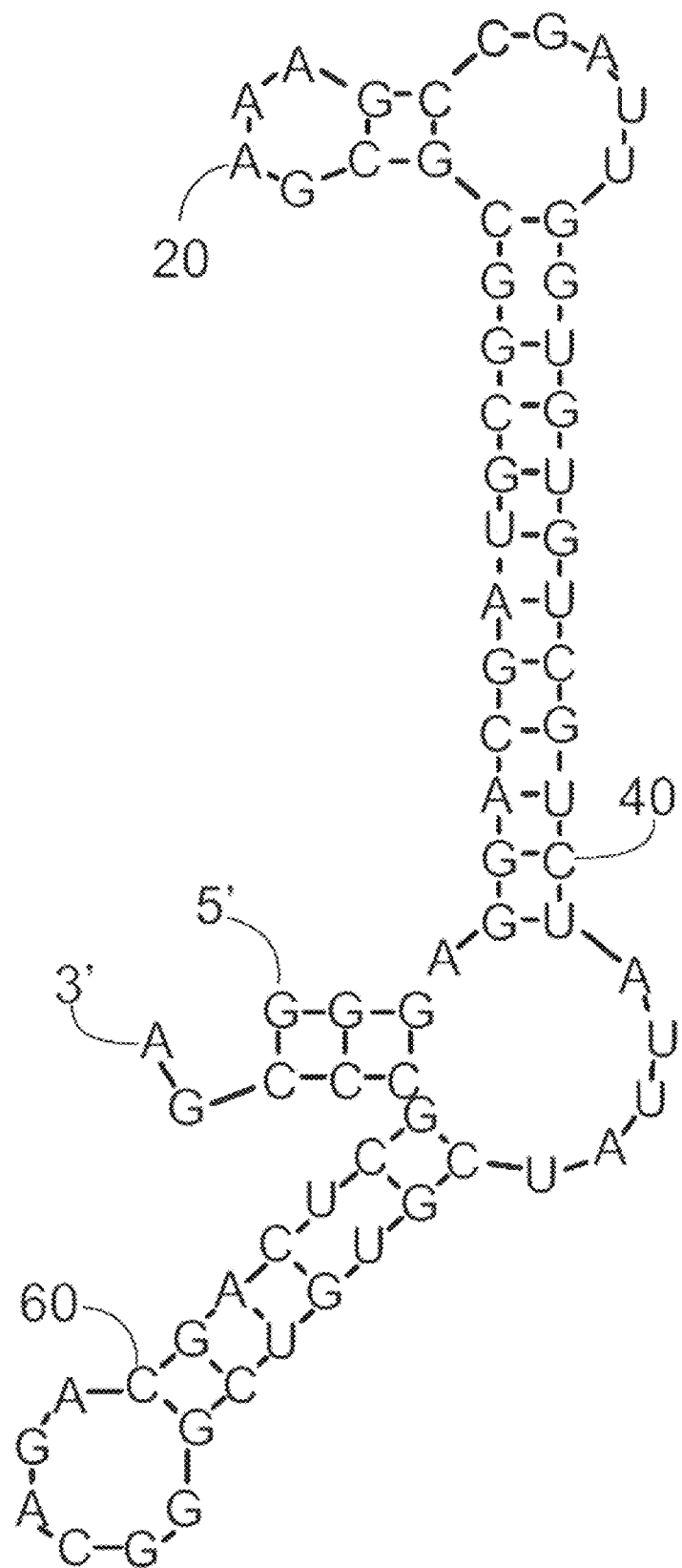
FIG. 2 is a representation of the secondary structure of Compound II as depicted with the nucleotide sequence set forth in SEQ ID NO:1. Other nucleotide sequences may have the 2-dimensional structure of Compound II including 2'-fluoropyrimidine-substituted variants of SEQ ID NO:1.
Figure 3:
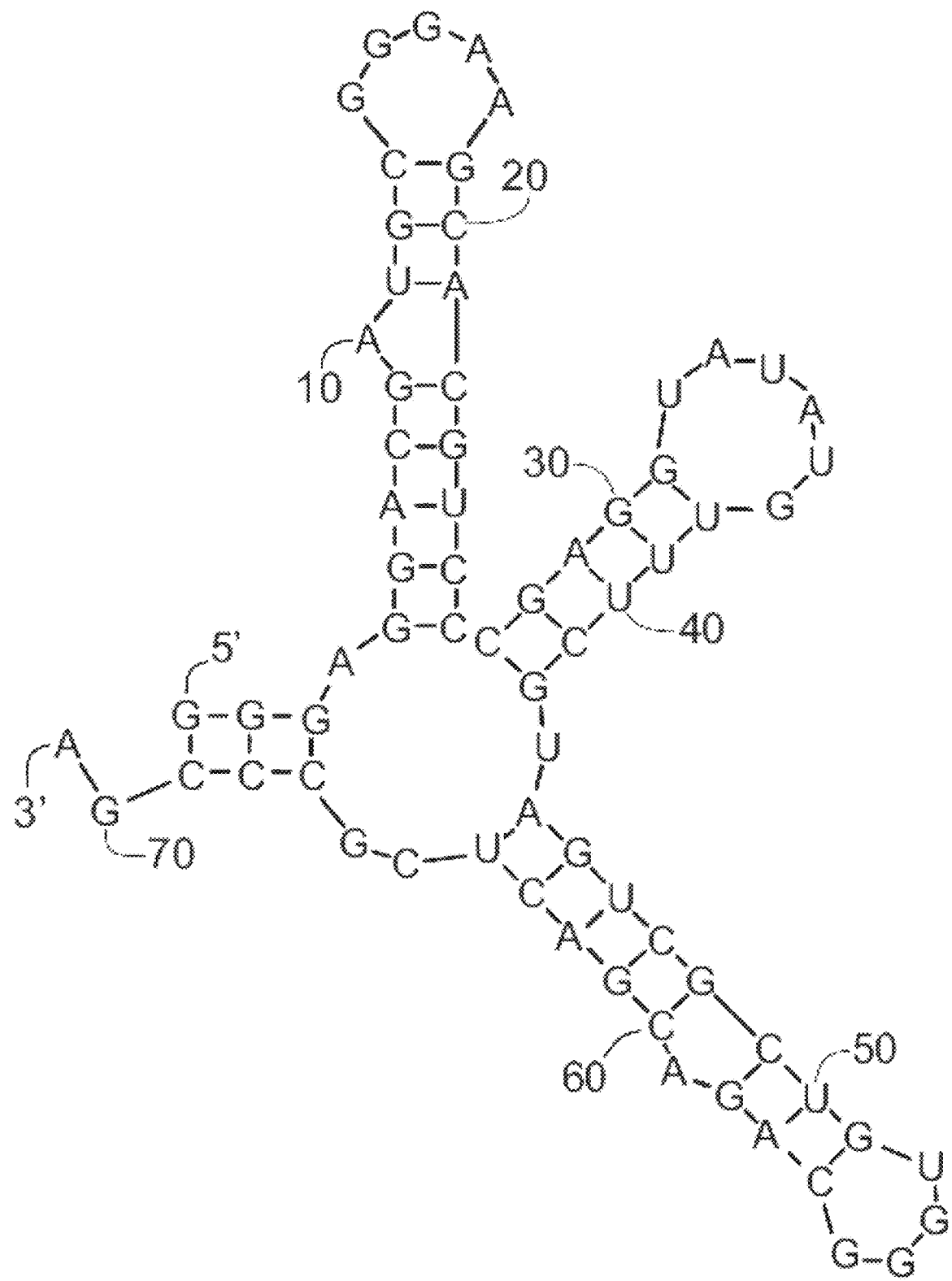
FIG. 3 is a representation of the secondary structure of Compound III as depicted with the nucleotide sequence set forth in SEQ ID NO:5. Other nucleotide sequences may have the 2-dimensional structure of Compound III including 2'-fluoropyrimidine-substituted variants of SEQ ID NO:5.
Figure 4:
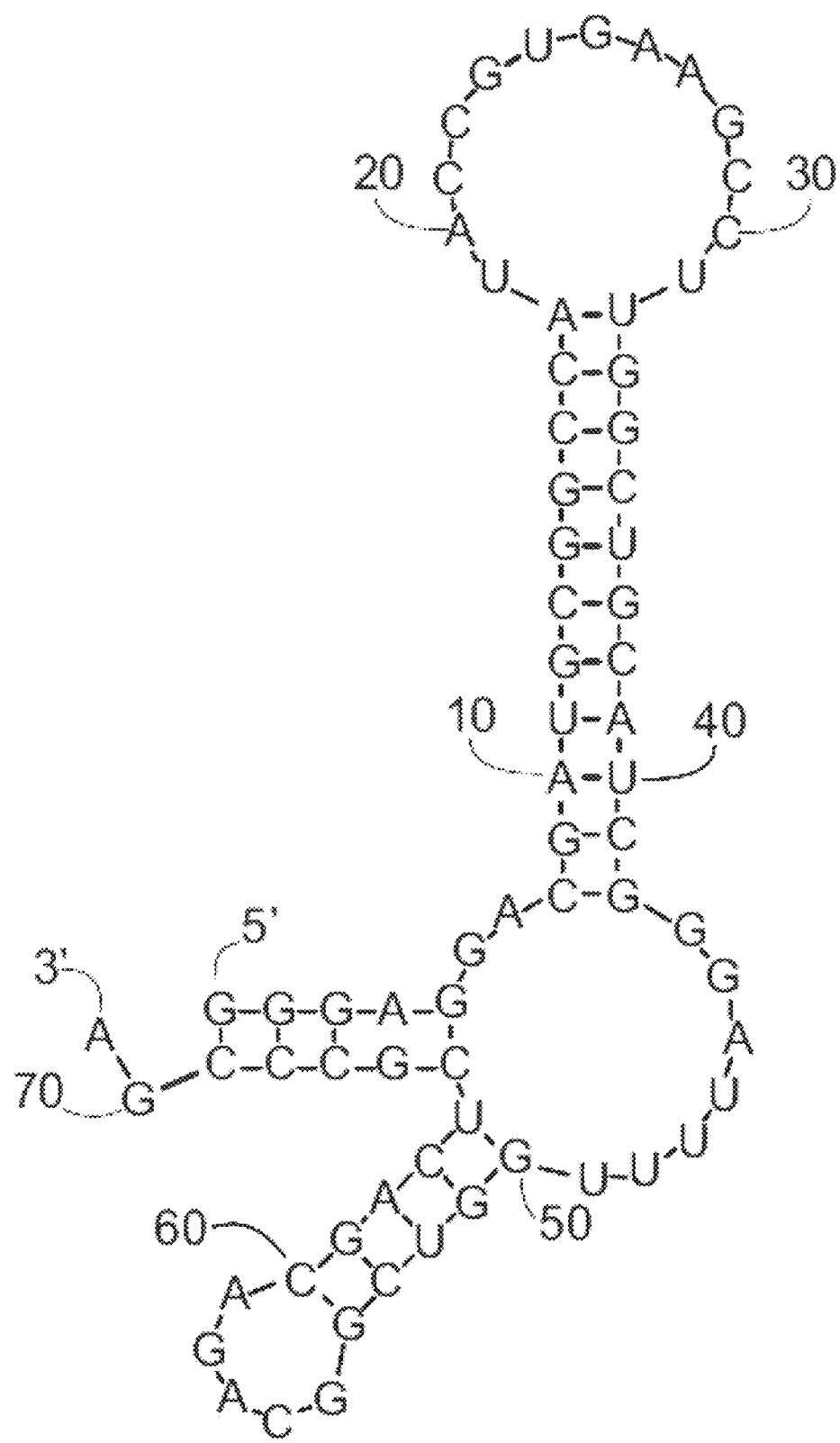
FIG. 4 is a representation of the secondary structure of Compound IV as depicted with the nucleotide sequence set forth in SEQ ID NO:7. Other nucleotide sequences may have the 2-dimensional structure of Compound IV including 2'-fluoropyrimidine-substituted variants of SEQ ID NO:7.

Some embodiments relate to an aptamer. In specific embodiments, the aptamer is a nucleic acid. In more specific embodiments, the aptamer comprises or consists of RNA. In more specific embodiments, the aptamer comprises a RNA nucleotide sequence. In very specific embodiments, the aptamer comprises one or more noncanonical nucleotides.

The term "noncanonical nucleotide" as utilized herein refers to a nucleotide other than adenosine monophosphate, deoxyadenosine monophosphate, cytidine monophosphate, deoxycytidine monophosphate, guanosine monophosphate, deoxyguanosine monophosphate, uridine monophosphate, and deoxythymidine monophosphate. The term "canonical nucleotide" as utilized herein refers to any one of adenosine monophosphate, deoxyadenosine monophosphate, cytidine monophosphate, deoxycytidine monophosphate, guanosine monophosphate, deoxyguanosine monophosphate, uridine monophosphate, and deoxythymidine monophosphate.

The term "RNA nucleotide sequence" as utilized herein refers to the nucleotide sequence of a ribonucleic acid polymer comprising canonical nucleotides and/or noncanonical nucleotides.

In some embodiments, the aptamer comprises nucleotides that form one or more intramolecular base pairs. In specific embodiments, the aptamer comprises a first nucleobase sequence and a second nucleobase sequence, the first nucleobase sequence and the second nucleobase sequence each comprise at least 4, 5, 6, 7, 8, 9, or 10 nucleobases, the first nucleobase sequence has at least 95% sequence homology with the reverse complement of the second nucleobase sequence, and the first nucleobase sequence and the second nucleobase sequence base-pair within the aptamer to form an intramolecular double strand.

In some embodiments, an aptamer comprises a nucleotide sequence having at least 70%, 80%, 85%, 90%, 95%, 96%, 97%, or 98% sequence identity with at least 24, 25, 30, 35, 39, 40, 45, 50, 55, 60, 65, 70, 75, 80, or 85 consecutive nucleotides of the nucleotide sequence set forth in SEQ ID NO:1. In specific embodiments, the aptamer comprises a nucleotide sequence having at least 95%, 96%, 97%, or 98% sequence identity with the nucleotide sequence set forth in SEQ ID NO:1. In very specific embodiments, the aptamer comprises the nucleotide sequence set forth in SEQ ID NO:1.

SEQ ID NO: 1
GGGAGGACGAUGCGGCGCGAAAGCCGAUUGGUGUGUCGUCUAUUAUCGUG
UCGGGCAGACGACUCGCCCGA

The term "sequence identity" as utilized herein refers to the percentage of exact nucleotide matches in a nucleotide sequence. Sequences are aligned using known methods prior to calculating sequence identity. Sequence alignments sometimes introduce one or more gaps into a nucleotide sequence to improve the alignment. The term "sequence identity" allows for the introduction of one or more gaps as long as the one or more gaps are introduced using the default parameters of a sequence alignment algorithm. A representative sequence alignment algorithm is Clustal Omega, and all sequence identity determinations according to the instant disclosure should be consistent with sequence alignments performed using relevant default parameters in Clustal Omega (http://www.clustal.org/omega; see also Sievers et al., Molecular Systems Biology, 2011, 7:539).

In some embodiments, an aptamer comprises a nucleobase sequence having at least 70%, 80%, 85%, 90%, 95%, 96%, 97%, or 98% nucleobase sequence identity with at least 24, 25, 30, 35, 39, 40, 45, 50, 55, 60, 65, 70, 75, 80, or 85 consecutive nucleotides of the nucleotide sequence set forth in SEQ ID NO:1. In specific embodiments, the aptamer comprises a nucleobase sequence having at least 95%, 96%, 97%, or 98% nucleobase sequence identity with the nucleotide sequence set forth in SEQ ID NO:1. In very specific embodiments, the aptamer comprises a nucleobase sequence having the same nucleobase sequence as the nucleotide sequence set forth in SEQ ID NO: 1.

In some embodiments, an aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in SEQ ID NO: 1. In specific embodiments, the aptamer comprises a nucleotide sequence comprising at least 95% sequence homology with the nucleotide sequence set forth in SEQ ID NO:1. In specific embodiments, the aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in SEQ ID NO:1, wherein no more than 30, 25, 20, 15, 14, 13, 12, 11, 10, 9, 8, 7, 6, 5, 4, 3, 2, or 1 nucleotides of the consecutive nucleotides are substituted with a noncanonical nucleotide (e.g., a 2'-fluoropyrimidine). In more specific embodiments, the aptamer comprises a nucleotide sequence comprising at least 95% sequence homology with the nucleotide sequence set forth in SEQ ID NO:1, wherein no more than 30, 25, 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with the nucleotide sequence set forth in SEQ ID NO:1.

The term "sequence homology" as utilized herein refers to the percentage of exact nucleobase matches in a nucleotide sequence. The term "nucleotide" is utilized herein in accordance to the art-recognized definition. A nucleotide comprises a five-carbon sugar, a phosphate, and either a pyrimidine or purine nucleobase. The term "nucleobase" is utilized herein in accordance to the art-recognized definition, i.e., a nucleobase is the pyrimidine or purine moiety of a nucleotide. Different nucleotide sequences can have the same nucleobase sequence. The nucleotide sequences C-C-C; dC-dC-dC; and 2FC-2FC-2FC, wherein "C" corresponds to cytidine, "dC" corresponds to 2'-deoxycytidine, "2FC" corresponds to 2'-fluoro-cytidine, and "-" corresponds to phosphate have 0% sequence identity and 100% sequence homology because their nucleotide sequences lack exact matches whereas their nucleobase sequences are exact matches. Sequences are aligned using known methods prior to calculating sequence homology. Sequence alignments sometimes introduce one or more gaps into a nucleotide sequence to improve the alignment. The term "sequence homology" allows for the introduction of one or more gaps as long as the one or more gaps are introduced using the default parameters of a sequence alignment algorithm. A representative sequence alignment algorithm is Clustal Omega, and all sequence homology determinations according to the instant disclosure should be consistent with sequence alignments performed using relevant default parameters in Clustal Omega (http://www.clustal.org/omega; see also Sievers et al., Molecular Systems Biology, 2011, 7:539).

Cytidine, deoxycytidine, 2'-halo-cytidine, 2'-halo-2'-deoxycytidine, 2'-fluoro-cytidine, 2'-fluoro-2'-deoxycytidine, 2'-amino-cytidine, 2'-amino-2'-deoxycytidine, 2'-O-alkyl-cytidine, 2'-O-alkyl-2'-deoxycytidine, 2'-O-methyl-cytidine, and 2'-O-methyl-2'-deoxycytidine all comprise the same nucleobase cytosine.

Uridine, deoxyuridine, 2'-halo-uridine, 2'-halo-2'-deoxyuridine, 2'-fluoro-uridine, 2'-fluoro-2'-deoxyuridine, 2'-amino-uridine, 2'-amino-2'-deoxyuridine, 2'-O-alkyl-uridine, 2'-O-alkyl-2'-deoxyuridine, 2'-O-methyl-uridine, and 2'-O-methyl-2'-deoxyuridine all comprise the same nucleobase uracil.

The term "2'-fluoropyrimidine" as utilized herein refers to a nucleotide comprising a pyrimidine nitrogenous base and a 5-carbon sugar that is fluoro-substituted at the 2' carbon. Examples of 2'-fluoropyrimidines include 2'-fluoro-cytidine monophosphate, 2'-fluoro-2'-deoxycytidine monophosphate, 2'-fluoro-uridine monophosphate, and 2'-fluoro-2'-deoxyuridine monophosphate.

In some embodiments, an aptamer comprises a nucleotide sequence comprising at least 95% sequence homology with the nucleotide sequence set forth in SEQ ID NO:2. In specific embodiments, the aptamer comprises a nucleotide sequence comprising at least 95% sequence homology with the nucleotide sequence set forth in SEQ ID NO:2, wherein no more than 6, 5, 4, 3, 2, or 1 nucleotides of the nucleotide sequence are substituted with a noncanonical nucleotide (e.g., a 2'-fluoropyrimidine). In more specific embodiments, the aptamer comprises a nucleotide sequence comprising at least 96%, 97%, 98%, 99% or 100% sequence homology with the nucleotide sequence set forth in SEQ ID NO:2. In more specific embodiments, the aptamer comprises a nucleotide sequence comprising at least 95% sequence identity with the nucleotide sequence set forth in SEQ ID NO:2. In very specific embodiments, the aptamer comprises the nucleotide sequence set forth in SEQ ID NO:2.

SEQ ID NO: 2
GGACGAUGCGGC

In some embodiments, an aptamer comprises a nucleobase sequence comprising at least 95% nucleobase sequence identity with the nucleotide sequence set forth in SEQ ID NO:2. In specific embodiments, the aptamer comprises a nucleobase sequence comprising at least 95% nucleobase sequence identity with the nucleotide sequence set forth in SEQ ID NO:2, wherein no more than 6, 5, 4, 3, 2, or 1 nucleotides of the nucleotide sequence are substituted with a noncanonical nucleotide (e.g., a 2'-fluoropyrimidine). In more specific embodiments, the aptamer comprises a nucleobase sequence comprising at least 96%, 97%, 98%, 99% or 100% nucleobase sequence identity with the nucleotide sequence set forth in SEQ ID NO:2. In more specific embodiments, the aptamer comprises a nucleobase sequence comprising at least 95% nucleobase sequence identity with the nucleotide sequence set forth in SEQ ID NO:2. In very specific embodiments, the aptamer comprises a nucleobase sequence having the same nucleobase sequence as the nucleotide sequence set forth in SEQ ID NO:2.

In some embodiments, an aptamer comprises a nucleotide sequence comprising at least 95% sequence homology with the nucleotide sequence set forth in SEQ ID NO:3. In specific embodiments, the aptamer comprises a nucleotide sequence comprising at least 95% sequence homology with the nucleotide sequence set forth in SEQ ID NO:3, wherein no more than 6, 5, 4, 3, 2, or 1 nucleotides of the nucleotide sequence are substituted with a noncanonical nucleotide (e.g., a 2'-fluoropyrimidine). In more specific embodiments, the aptamer comprises a nucleotide sequence comprising at least 96%, 97%, 98%, 99% or 100% sequence homology with the nucleotide sequence set forth in SEQ ID NO:3. In more specific embodiments, the aptamer comprises a nucleotide sequence comprising at least 95% sequence identity with the nucleotide sequence set forth in SEQ ID NO:3. In very specific embodiments, the aptamer comprises the nucleotide sequence set forth in SEQ ID NO:3.

SEQ ID NO: 3
GGUGUGUCGUCU

In some embodiments, an aptamer comprises a nucleobase sequence comprising at least 95% nucleobase sequence identity with the nucleotide sequence set forth in SEQ ID NO:3. In specific embodiments, the aptamer comprises a nucleobase sequence comprising at least 95% nucleobase sequence identity with the nucleotide sequence set forth in SEQ ID NO:3, wherein no more than 6, 5, 4, 3, 2, or 1 nucleotides of the nucleotide sequence are substituted with a noncanonical nucleotide (e.g., a 2'-fluoropyrimidine). In more specific embodiments, the aptamer comprises a nucleobase sequence comprising at least 96%, 97%, 98%, 99% or 100% nucleobase sequence identity with the nucleotide sequence set forth in SEQ ID NO:3. In more specific embodiments, the aptamer comprises a nucleotide sequence comprising at least 95% nucleobase sequence identity with the nucleotide sequence set forth in SEQ ID NO:3. In very specific embodiments, the aptamer comprises a nucleobase sequence having the same nucleobase sequence as the nucleotide sequence set forth in SEQ ID NO:3.

In some embodiments, an aptamer comprises a nucleotide sequence having at least 70%, 80%, 85%, 90%, 95%, 96%, 97%, or 98% sequence identity with at least 24, 25, 30, or 35 consecutive nucleotides of the nucleotide sequence set forth in SEQ ID NO:4. In specific embodiments, the aptamer comprises a nucleotide sequence having at least 95%, 96%, 97%, or 98% sequence identity with the nucleotide sequence set forth in SEQ ID NO:4. In very specific embodiments, the aptamer comprises the nucleotide sequence set forth in SEQ ID NO:4.

SEQ ID NO: 4
CGCGAAAGCCGAUUGGUGUGUCGUCUAUUAUCGUG

In some embodiments, an aptamer comprises a nucleobase sequence having at least 70%, 80%, 85%, 90%, 95%, 96%, 97%, or 98% nucleobase sequence identity with at least 24, 25, 30, or 35 consecutive nucleotides of the nucleotide sequence set forth in SEQ ID NO:4. In specific embodiments, the aptamer comprises a nucleobase sequence having at least 95%, 96%, 97%, or 98% nucleobase sequence identity with the nucleotide sequence set forth in SEQ ID NO:4. In very specific embodiments, the aptamer comprises a nucleobase sequence having the same nucleobase sequence as the nucleotide sequence set forth in SEQ ID NO:4.

In some embodiments, an aptamer comprises a nucleotide sequence comprising at least 95% sequence homology with at least 24, 25, 30, or 35 consecutive nucleotides of the nucleotide sequence set forth in SEQ ID NO:4. In specific embodiments, the aptamer comprises a nucleotide sequence comprising at least 95% sequence homology with the nucleotide sequence set forth in SEQ ID NO:4. In specific embodiments, the aptamer comprises a nucleotide sequence comprising at least 95% sequence homology with at least 24, 25, 30, or 35 consecutive nucleotides of the nucleotide sequence set forth in SEQ ID NO:4, wherein no more than 20, 15, 14, 13, 12, 11, 10, 9, 8, 7, 6, 5, 4, 3, 2, or 1 nucleotides of the consecutive nucleotides are substituted with a non-canonical nucleotide (e.g., a 2'-fluoropyrimidine). In more specific embodiments, the aptamer comprises a nucleotide sequence comprising at least 95% sequence homology with the nucleotide sequence set forth in SEQ ID NO:4, wherein no more than 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with the nucleotide sequence set forth in SEQ ID NO:4.

In some embodiments, an aptamer comprises one or more of SEQ ID NO:2, SEQ ID NO:3, and SEQ ID NO:4. In specific embodiments, the aptamer comprises SEQ ID NO:2 and SEQ ID NO:3, and the nucleotides of SEQ ID NO:2 form a double strand with the nucleotides of SEQ ID NO:3. In very specific embodiments, the aptamer comprises SEQ ID NO:2 and SEQ ID NO:3, the nucleotides of SEQ ID NO:2 form a double strand with the nucleotides of SEQ ID NO:3, and the double strand comprises one or more wobble base pairs.

The term "wobble base pair" as utilized herein refers to a base pair comprising two hydrogen bonds, wherein the base pair is not an adenine-thymine, adenine-uracil, or guanine-cytosine base pair. An example of a wobble base pair is a guanine-uracil base pair. In specific embodiments, the aptamer comprises secondary structure comprising one or more guanine-uracil base pairs.

In some embodiments, an aptamer comprises a nucleotide sequence having at least 70%, 80%, 85%, 90%, 95%, 96%, 97%, or 98% sequence identity with at least 24, 25, 30, 35, 39, 40, 45, 50, 55, 60, 65, or 70 consecutive nucleotides of the nucleotide sequence set forth in SEQ ID NO:5. In specific embodiments, the aptamer comprises a nucleotide sequence having at least 95%, 96%, 97%, or 98% sequence identity with the nucleotide sequence set forth in SEQ ID NO:5. In very specific embodiments, the aptamer comprises the nucleotide sequence set forth in SEQ ID NO:5.

SEQ ID NO: 5
GGGAGGACGAUGCGGGAAGCACGUCCCGAGGUAUAUGUUUCGUAGUCGCU
GUGGGCAGACGACUCGCCCGA

In some embodiments, an aptamer comprises a nucleobase sequence having at least 70%, 80%, 85%, 90%, 95%, 96%, 97%, or 98% nucleobase sequence identity with at least 24, 25, 30, 35, 39, 40, 45, 50, 55, 60, 65, or 70 consecutive nucleotides of the nucleotide sequence set forth in SEQ ID NO:5. In specific embodiments, the aptamer comprises a nucleobase sequence having at least 95%, 96%, 97%, or 98% nucleobase sequence identity with the nucleotide sequence set forth in SEQ ID NO:5. In very specific embodiments, the aptamer comprises a nucleobase sequence having the same nucleobase sequence as the nucleotide sequence set forth in SEQ ID NO:5.

In some embodiments, an aptamer comprises a nucleotide sequence comprising at least 95% sequence homology with at least 24, 25, 30, 35, 39, 40, 45, 50, 55, 60, 65, 70, 75, 80, or 85 consecutive nucleotides of the nucleotide sequence set forth in SEQ ID NO:5. In specific embodiments, the aptamer comprises a nucleotide sequence comprising at least 95% sequence homology with the nucleotide sequence set forth in SEQ ID NO:5. In specific embodiments, the aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in SEQ ID NO:5, wherein no more than 30, 25, 20, 15, 14, 13, 12, 11, 10, 9, 8, 7, 6, 5, 4, 3, 2, or 1 nucleotides of the consecutive nucleotides are substituted with a noncanonical nucleotide (e.g., a 2'-fluoropyrimidine). In more specific embodiments, the aptamer comprises a nucleotide sequence comprising at least 95% sequence homology with the nucleotide sequence set forth in SEQ ID NO:5, wherein no more than 25, 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100%/sequence homology with the nucleotide sequence set forth in SEQ ID NO:5.

In some embodiments, an aptamer comprises a nucleotide sequence having at least 70%, 80%, 85%, 90%, 95%, 96%, 97%, or 98% sequence identity with at least 24, 30, 31, 32, 33, or 34 consecutive nucleotides of the nucleotide sequence set forth in SEQ ID NO:6. In specific embodiments, the aptamer comprises a nucleotide sequence having at least 95%, 96%, 97%, or 98% sequence identity with the nucleotide sequence set forth in SEQ ID NO:6. In very specific embodiments, the aptamer comprises the nucleotide sequence set forth in SEQ ID NO:6.

SEQ ID NO: 6
GAAGCACGUCCCGAGGUAUAUGUUUCGUAGUCGCU

In some embodiments, an aptamer comprises a nucleobase sequence having at least 70%, 80%, 85%, 90%, 95%, 96%, 97%, or 98% nucleobase sequence identity with at least 24, 30, 31, 32, 33, or 34 consecutive nucleotides of the nucleotide sequence set forth in SEQ ID NO:6. In specific embodiments, the aptamer comprises a nucleobase sequence having at least 95%, 96%, 97%, or 98% nucleobase sequence identity with the nucleotide sequence set forth in SEQ ID NO:6. In very specific embodiments, the aptamer comprises a nucleobase sequence having the same nucleobase sequence as the nucleotide sequence set forth in SEQ ID NO:6.

In some embodiments, an aptamer comprises a nucleotide sequence comprising at least 95% sequence homology with at least 24, 30, 31, 32, 33, or 34 consecutive nucleotides of the nucleotide sequence set forth in SEQ ID NO:6. In specific embodiments, the aptamer comprises a nucleotide sequence comprising at least 95% sequence homology with the nucleotide sequence set forth in SEQ ID NO:6. In specific embodiments, the aptamer comprises a nucleotide sequence comprising at least 95% sequence homology with at least 24, 30, 31, 32, 33, or 34 consecutive nucleotides of the nucleotide sequence set forth in SEQ ID NO:6, wherein no more than 20, 15, 14, 13, 12, 11, 10, 9, 8, 7, 6, 5, 4, 3, 2, or 1 nucleotides of the consecutive nucleotides are substituted with a noncanonical nucleotide (e.g., a 2'-fluoropyrimidine). In more specific embodiments, the aptamer comprises a nucleotide sequence comprising at least 95% sequence homology with the nucleotide sequence set forth in SEQ ID NO:6, wherein no more than 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with the nucleotide sequence set forth in SEQ ID NO:6.

In some embodiments, an aptamer comprises a nucleotide sequence having at least 70%, 80%, 85%, 90%, 95%, 96%, 97%, or 98% sequence identity with at least 24, 25, 30, 35, 39, 40, 45, 50, 55, 60, 65, or 70 consecutive nucleotides of the nucleotide sequence set forth in SEQ ID NO:7. In specific embodiments, the aptamer comprises a nucleotide sequence having at least 95%, 96%, 97%, or 98% sequence identity with the nucleotide sequence set forth in SEQ ID NO:7. In very specific embodiments, the aptamer comprises the nucleotide sequence set forth in SEQ ID NO:7.

SEQ ID NO: 7
GGGAGGACGAUGCGGCCAUACCGUGAAGCCUUGGCUGCAUCGGGAUUUUG
GUCGGCAGACGACUCGCCCGA

In some embodiments, an aptamer comprises a nucleobase sequence having at least 70%, 80%, 85%, 90%, 95%, 96%, 97%, or 98% nucleobase sequence identity with at least 24, 25, 30, 35, 39, 40, 45, 50, 55, 60, 65, or 70 consecutive nucleotides of the nucleotide sequence set forth in SEQ ID NO:7. In specific embodiments, the aptamer comprises a nucleobase sequence having at least 95%, 96%, 97%, or 98% nucleobase sequence identity with the nucleotide sequence set forth in SEQ ID NO:7. In very specific embodiments, the aptamer comprises a nucleobase sequence having the same nucleobase sequence as the nucleotide sequence set forth in SEQ ID NO:7.

In some embodiments, an aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in SEQ ID NO:7. In specific embodiments, the aptamer comprises a nucleotide sequence comprising at least 95% sequence homology with the nucleotide sequence set forth in SEQ ID NO:7. In specific embodiments, the aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in SEQ ID NO:7, wherein no more than 35, 30, 25, 20, 15, 14, 13, 12, 11, 10, 9, 8, 7, 6, 5, 4, 3, 2, or 1 nucleotides of the consecutive nucleotides are substituted with a noncanonical nucleotide (e.g., a 2'-fluoropyrimidine). In more specific embodiments, the aptamer comprises a nucleotide sequence comprising at least 95% sequence homology with the nucleotide sequence set forth in SEQ ID NO:7, wherein no more than 35, 30, 25, 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with the nucleotide sequence set forth in SEQ ID NO:7.

In some embodiments, an aptamer comprises a nucleotide sequence having at least 70%, 80%, 85%, 90%, 95%, 96%, 97%, or 98% sequence identity with at least 24, 30, 31, 32, 33, or 34 consecutive nucleotides of the nucleotide sequence set forth in SEQ ID NO:8. In specific embodiments, the aptamer comprises a nucleotide sequence having at least 95%, 96%, 97%, or 98% sequence identity with the nucleotide sequence set forth in SEQ ID NO:8. In very specific embodiments, the aptamer comprises the nucleotide sequence set forth in SEQ ID NO:8.

SEQ ID NO: 8
CCAUACCGUGAAGCCUUGGCUGCAUCGGGAUUUUG

In some embodiments, an aptamer comprises a nucleobase sequence having at least 70%, 80%, 85%, 90%, 95%, 96%, 97%, or 98% nucleobase sequence identity with at least 24, 30, 31, 32, 33, or 34 consecutive nucleotides of the nucleotide sequence set forth in SEQ ID NO:8. In specific embodiments, the aptamer comprises a nucleobase sequence having at least 95%, 96%, 97%, or 98% nucleobase sequence identity with the nucleotide sequence set forth in SEQ ID NO:8. In very specific embodiments, the aptamer comprises a nucleobase sequence having the same nucleobase sequence as the nucleotide sequence set forth in SEQ ID NO:8.

In some embodiments, an aptamer comprises a nucleotide sequence comprising at least 95% sequence homology with at least 24, 30, 31, 32, 33, or 34 consecutive nucleotides of the nucleotide sequence set forth in SEQ ID NO:8. In specific embodiments, the aptamer comprises a nucleotide sequence comprising at least 95% sequence homology with the nucleotide sequence set forth in SEQ ID NO:8. In specific embodiments, the aptamer comprises a nucleotide sequence comprising at least 95% sequence homology with at least 24, 30, 31, 32, 33, or 34 consecutive nucleotides of the nucleotide sequence set forth in SEQ ID NO:8, wherein no more than 20, 15, 14, 13, 12, 11, 10, 9, 8, 7, 6, 5, 4, 3, 2, or 1 nucleotides of the consecutive nucleotides are substituted with a noncanonical nucleotide (e.g., a 2'-fluoropyrimidine). In more specific embodiments, the aptamer comprises a nucleotide sequence comprising at least 95% sequence homology with the nucleotide sequence set forth in SEQ ID NO:8, wherein no more than 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with the nucleotide sequence set forth in SEQ ID NO:8.

In some embodiments, an aptamer comprises a nucleotide sequence having at least 70%, 80%, 85%, 90%, 95%, 96%, 97%, or 98% sequence identity with at least 24, 25, 30, 35, 39, 40, 45, 50, 55, 60, 65, or 70 consecutive nucleotides of the nucleotide sequence set forth in any one of SEQ ID NO:9 to SEQ ID NO:76. In specific embodiments, the aptamer comprises a nucleobase sequence having at least 95%, 96%, 97%, or 98% sequence identity with the nucleotide sequence set forth in any one of SEQ ID NO:9 to SEQ ID NO:76. In very specific embodiments, the aptamer comprises the nucleotide sequence set forth in any one of SEQ ID NO:9 to SEQ ID NO:76.

In some embodiments, an aptamer comprises a nucleobase sequence having at least 70%, 80%, 85%, 90%, 95%, 96%, 97%, or 98% nucleobase sequence identity with at least 24, 25, 30, 35, 39, 40, 45, 50, 55, 60, 65, or 70 consecutive nucleotides of the nucleotide sequence set forth in any one of SEQ ID NO:9 to SEQ ID NO:76. In specific embodiments, the aptamer comprises a nucleobase sequence having at least 95%, 96%, 97%, or 98% nucleobase sequence identity with the nucleotide sequence set forth in any one of SEQ ID NO:9 to SEQ ID NO:76. In very specific embodiments, the aptamer comprises a nucleobase sequence having the same nucleobase sequence as the nucleotide sequence set forth in any one of SEQ ID NO:9 to SEQ ID NO:76.

In some embodiments, an aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in any one of SEQ ID NO:9 to SEQ ID NO:76. In specific embodiments, the aptamer comprises a nucleotide sequence comprising at least 95% sequence homology with the nucleotide sequence set forth in any one of SEQ ID NO:9 to SEQ ID NO:76. In specific embodiments, the aptamer comprises a nucleotide sequence comprising at least 95% sequence homology with at least 24, 25, 30, 35, 39, 40, 45, 50, 55, 60, 65, or 70 consecutive nucleotides of the nucleotide sequence set forth in any one of SEQ ID NO:9 to SEQ ID NO:76, wherein no more than 35, 30, 25, 20, 15, 14, 13, 12, 11, 10, 9, 8, 7, 6, 5, 4, 3, 2, or 1 nucleotides of the consecutive nucleotides are substituted with a noncanonical nucleotide (e.g., a 2'-fluoropyrimidine). In more specific embodiments, the aptamer comprises a nucleotide sequence comprising at least 95% sequence homology with the nucleotide sequence set forth in any one of SEQ ID NO:9 to SEQ ID NO:76, wherein no more than 35, 30, 25, 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with the nucleotide sequence set forth in any one of SEQ ID NO:9 to SEQ ID NO:76.

In some embodiments, an aptamer comprises a nucleotide sequence having at least 70%, 80%, 85%, 90%, 95%, 96%, 97%, or 98% sequence identity with nucleotides 33 to 73 of the nucleotide sequence set forth in any one of SEQ ID NO:9 to SEQ ID NO:76. In specific embodiments, the aptamer comprises a nucleotide sequence having at least 95%, 96%, 97%, or 98% sequence identity with nucleotides 33 to 73 of the nucleotide sequence set forth in any one of SEQ ID NO:9 to SEQ ID NO:76. In very specific embodiments, the aptamer comprises a nucleotide sequence corresponding to nucleotides 33 to 73 of the nucleotide sequence set forth in any one of SEQ ID NO:9 to SEQ ID NO:76.

In some embodiments, an aptamer comprises a nucleobase sequence having at least 70%, 80%, 85%, 90%, 95%, 96%, 97%, or 98% nucleobase sequence identity with nucleotides 33 to 73 of the nucleotide sequence set forth in any one of SEQ ID NO:9 to SEQ ID NO:76. In specific embodiments, the aptamer comprises a nucleobase sequence having at least 95%, 96%, 97%, or 98% nucleobase sequence identity with nucleotides 33 to 73 of the nucleotide sequence set forth in any one of SEQ ID NO:9 to SEQ ID NO:76. In very specific embodiments, the aptamer comprises a nucleobase sequence corresponding to nucleotides 33 to 73 of the nucleotide sequence set forth in any one of SEQ ID NO:9 to SEQ ID NO:76.

In some embodiments, an aptamer comprises a nucleotide sequence comprising at least 95% sequence homology with nucleotides 33 to 73 of the nucleotide sequence set forth in any one of SEQ ID NO:9 to SEQ ID NO:76. In specific embodiments, the aptamer comprises a nucleotide sequence comprising at least 95% sequence homology with nucleotides 33 to 73 of the nucleotide sequence set forth in any one of SEQ ID NO:9 to SEQ ID NO:76, wherein no more than 25, 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In more specific embodiments, the aptamer comprises a nucleotide sequence comprising at least 95% sequence homology with nucleotides 33 to 73 of the nucleotide sequence set forth in any one of SEQ ID NO:9 to SEQ ID NO:76, wherein no more than 20, 15, 14, 13, 12, 11, 10, 9, 8, 7, 6, 5, 4, 3, 2, or 1 nucleotides of the nucleotide sequence are substituted with a noncanonical nucleotide (e.g., a 2'-fluoropyrimidine). In very specific embodiments, the aptamer comprises a nucleotide sequence comprising at least 96%, 97%, 98%, 99% or 100% sequence homology with nucleotides 33 to 73 of the nucleotide sequence set forth in any one of SEQ ID NO:9 to SEQ ID NO:76.

In some embodiments, an aptamer comprises one or more noncanonical nucleotides. In specific embodiments, the one or more noncanonical nucleotides comprise halogenated nucleotide(s). In more specific embodiments, the one or more noncanonical nucleotides comprise one or more of 2'-halo-uridine monophosphate, 2'-fluoro-uridine monophosphate, 2'-amino-uridine monophosphate, 2'-O-alkyl-uridine monophosphate, 2'-O-methyl-uridine monophosphate, 2'-halo-cytidine monophosphate, 2'-fluoro-cytidine monophosphate, 2'-amino-cytidine monophosphate, 2'-O-methyl-cytidine monophosphate, 2'-O-alkyl-cytidine monophosphate, 2'-halo-2'-deoxyuridine monophosphate, 2'-fluoro-2'-deoxyuridine monophosphate, 2'-amino-2'-deoxyuridine monophosphate, 2'-O-alkyl-2'-deoxyuridine monophosphate, 2'-O-methyl-2'-deoxyuridine monophosphate, 2'-halo-2'-deoxycytidine monophosphate, 2'-fluoro-2'-deoxycytidine monophosphate, 2'-amino-2'-deoxycytidine monophosphate, 2'-O-methyl-2'-deoxycytidine monophosphate, 2'-O-alkyl-2'-deoxycytidine monophosphate. In more specific embodiments, the one or more noncanonical nucleotides comprise 2'-fluoropyrimidine monophosphate. In very specific embodiments, the one or more noncanonical nucleotides comprise 2'-fluoro-uridine monophosphate, 2'-fluoro-2'-deoxyuridine monophosphate, 2'-fluoro-cytidine monophosphate, or 2'-fluoro-2'-deoxycytidine monophosphate.

In some embodiments, an aptamer comprises 95% sequence homology with the nucleotide sequence set forth in SEQ ID NO:1, and the aptamer comprises the secondary structure of Compound I or Compound II. In specific embodiments, the aptamer comprises 100% sequence homology with the nucleotide sequence set forth in SEQ ID NO:1, and the aptamer comprises the secondary structure of Compound I or Compound II. In more specific embodiments, the aptamer comprises 95% sequence identity with the nucleotide sequence set forth in SEQ ID NO:1, and the aptamer comprises the secondary structure of Compound I or Compound II. In very specific embodiments, the aptamer comprises 100% sequence identity with the nucleotide sequence set forth in SEQ ID NO:1, and the aptamer comprises the secondary structure of Compound I or Compound II.

The term "secondary structure" as utilized herein refers to a pattern of base pairing between the nucleobases of a nucleic acid. Two aptamers comprise the same secondary structure, for example, if the two aptamers comprise the same nucleobase sequence, and if the nucleobases of each aptamer form the same pattern of base pairs in each aptamer. The substitution of cytidine 40 of Compound I with 2'-fluoro-2'-deoxycytidine can result in an aptamer with the same secondary structure as Compound I, for example, because both cytidine and 2'-fluoro-cytidine can base pair with guanosine 6, e.g., because cytidine and 2'-fluoro-2'-deoxycytidine comprise the same nucleobase cytosine. Two aptamers may therefore comprise the same nucleobase sequence, different nucleotide sequences, and the same secondary structure. Two aptamers comprise the same secondary structure, for example, even if the two aptamers comprise different nucleobase sequences if the different nucleobase sequences nevertheless result in the same pattern of base pairing. The substitution of guanosine 6 and cytidine 40 of Compound I with adenosine and uridine can result in an aptamer with the same secondary structure as Compound I, for example, because guanosine 6 and cytidine 40 form a base pair in Compound I, and adenosine and uridine can also form a base pair. Two aptamers may therefore comprise the different nucleobase sequences, different nucleotide sequences, and the same secondary structure.

In some embodiments, an aptamer comprises 95% sequence homology with the nucleotide sequence set forth in SEQ ID NO:5, and the aptamer comprises the secondary structure of Compound III. In specific embodiments, the aptamer comprises 100% sequence homology with the nucleotide sequence set forth in SEQ ID NO:5, and the aptamer comprises the secondary structure of Compound III. In more specific embodiments, the aptamer comprises 95% sequence identity with the nucleotide sequence set forth in SEQ ID NO:5, and the aptamer comprises the secondary structure of Compound III. In very specific embodiments, the aptamer comprises 100% sequence identity with the nucleotide sequence set forth in SEQ ID NO:5, and the aptamer comprises the secondary structure of Compound III.

In some embodiments, an aptamer comprises 95% sequence homology with the nucleotide sequence set forth in SEQ ID NO:7, and the aptamer comprises the secondary structure of Compound IV. In specific embodiments, the aptamer comprises 100% sequence homology with the nucleotide sequence set forth in SEQ ID NO:7, and the aptamer comprises the secondary structure of Compound IV. In more specific embodiments, the aptamer comprises 95% sequence identity with the nucleotide sequence set forth in SEQ ID NO:7, and the aptamer comprises the secondary structure of Compound IV. In very specific embodiments, the aptamer comprises 100% sequence identity with the nucleotide sequence set forth in SEQ ID NO:7, and the aptamer comprises the secondary structure of Compound IV.

In some embodiments, an aptamer comprises secondary structure comprising one or more wobble base pairs.

In some embodiments, an aptamer specifically binds Müllerian inhibitory substance II receptor (MISIIR). In specific embodiments, the aptamer specifically binds human MISIIR. In specific embodiments, the aptamer specifically binds the extracellular domain of MISIIR. In very specific embodiments, the aptamer specifically binds the extracellular domain of human MISIIR.

The term "specifically binds" as utilized herein refers to an interaction that has a dissociation constant of 10 µM or less at neutral pH, 70±5° F., and physiological ion strength such as phosphate buffered saline. A dissociation constant may be determined, for example, by surface plasmon resonance or immunoassay according to known methods.

In some embodiments, an aptamer specifically binds MISIIR with a dissociation constant of less than 5 µM, 2 µM, 1 µM, 500 nM, 200 nM, 100 nM, 50 nM, 20 nM, 10 nM, or 5 nM. In specific embodiments, the aptamer specifically binds MISIIR with a dissociation constant of less than 50 nM.

In some embodiments, an aptamer specifically binds human MISIIR with a dissociation constant of less than 5 µM, 2 µM, 1 µM, 500 nM, 200 nM, 100 nM, 50 nM, 20 nM, 10 nM, or 5 nM. In specific embodiments, the aptamer specifically binds human MISIIR with a dissociation constant of less than 50 nM.

In some embodiments, an aptamer specifically binds the extracellular domain of MISIIR with a dissociation constant of less than 5 µM, 2 µM, 1 µM, 500 nM, 200 nM, 100 nM, 50 nM, 20 nM, 10 nM, or 5 nM. In specific embodiments, the aptamer specifically binds the extracellular domain of MISIIR with a dissociation constant of less than 50 nM.

In some embodiments, an aptamer specifically binds the extracellular domain of human MISIIR with a dissociation constant of less than 5 µM, 2 µM, 1 µM, 500 nM, 200 nM, 100 nM, 50 nM, 20 nM, 10 nM, or 5 nM. In specific embodiments, the aptamer specifically binds the extracellular domain of human MISIIR with a dissociation constant of less than 50 nM.

In some embodiments, an aptamer specifically binds cells that express MISIIR with a dissociation constant of less than 5 µM, 2 µM, 1 µM, 500 nM, 200 nM, 100 nM, 50 nM, 20 nM, 10 nM, or 5 nM. In specific embodiments, the aptamer specifically binds cells that express MISIIR with a dissociation constant of less than 50 nM.

In some embodiments, an aptamer specifically binds cells that express human MISIIR with a dissociation constant of less than 5 µM, 2 µM, 1 µM, 500 nM, 200 nM, 100 nM, 50 nM, 20 nM, 10 nM, or 5 nM. In specific embodiments, the aptamer specifically binds cells that express human MISIIR with a dissociation constant of less than 50 nM.

In some embodiments, an aptamer does not bind cells that lack MISIIR with a dissociation constant less than 100 nM, 200 nM, 500 nM, 1 µM, 2 µM, 5 µM, 10 µM, 20 µM, 50 µM, 100 µM, 200 µM, 500 µM, or 1 mM. In specific embodiments, the aptamer does not bind cells that lack MISIIR with a dissociation constant less than 50 µM.

In some embodiments, an aptamer is capable of binding a cell that expresses MISIIR and inducing endocytosis by the cell.

In some embodiments, an aptamer is covalently bound to another molecule, i.e., the aptamer is an aptamer of an aptamer conjugate.

Some embodiments relate to an aptamer conjugate. The term "aptamer conjugate" as utilized herein refers to an aptamer that is covalently bound to another molecule.

In some embodiments, an aptamer conjugate is an aptamer-drug conjugate. In specific embodiments, the aptamer conjugate comprises an aptamer and a pharmaceutical agent. In more specific embodiments, the pharmaceutical agent is a siRNA, microRNA, a chemotherapeutic agent, a photosensitizing agent, a photothermal agent, an immunotherapeutic agent, a radiopharmaceutical agent, or an enzyme. In more specific embodiments, the aptamer is conjugated to a siRNA or microRNA. Suitable pharmaceutical agents and methods of conjugating pharmaceutical agents to aptamers are described, for example, in PCT Patent Application Publication No. WO2017173247A1, which is hereby incorporated by reference in its entirety. In very specific embodiments, the aptamer is conjugated to siRNA. In very specific embodiments, the siRNA sensitizes cancer cells to cisplatin.

In some embodiments, an aptamer conjugate is pegylated.

Some embodiments relate to a nucleic acid comprising a DNA nucleotide sequence encoding an aptamer described herein.

In some embodiments, a nucleic acid comprises a DNA nucleotide sequence encoding both an aptamer described herein and a pharmaceutical agent, wherein the pharmaceutical agent is RNA. In specific embodiments, the pharmaceutical agent is siRNA or microRNA. In specific embodiments, the DNA nucleotide sequence is configured such that the transcription of the DNA nucleotide sequence encoding both the aptamer described herein and the pharmaceutical agent produces a single RNA transcript comprising both the aptamer and the pharmaceutical agent.

In some embodiments, a nucleic acid further comprises a promoter, wherein the promoter is operably-linked to a DNA nucleotide sequence encoding an aptamer described herein. In specific embodiments, the promoter is capable of driving constitutive or inducible expression of the nucleotide sequence encoding the aptamer described herein.

The term "operably-linked" as utilized herein means that a transcription regulatory element is capable of mediating transcription of the nucleotide sequence to which the transcription regulatory element is operably-linked. The term "transcription regulatory element" as utilized herein refers to nucleotide sequences that are capable of binding a promoter or transcription factor to thereby mediate the transcription of a nucleotide sequence. Examples of transcription regulatory elements include promoters, enhancers, and silencers.

In some embodiments, a nucleic acid comprising a DNA nucleotide sequence as described herein is a plasmid. In specific embodiments, the nucleic acid comprises an origin of replication. In more specific embodiments, the origin of replication is an origin of replication of a prokaryotic cell. In very specific embodiments, the origin of replication is an *Escherichia coli* origin of replication.

Some embodiments relate to a cell comprising a nucleic acid comprising a DNA nucleotide sequence encoding an aptamer described herein. In specific embodiments, the cell is a cloning cell or an expression cell. In very specific embodiments, the cell is a cloning cell, and the cell is *Escherichia coli*. In very specific embodiments, the cell is an expression cell, and the cell is selected from *Escherichia coli, Saccharomyces cerevisiae, Pichia Pastoris*, Sf9, Sf21, BTI-Tn-5B1-4, CHO, HEK, COS, HeLA, and Jurkat cells.

Some embodiments relate to a method of treating a subject, comprising administering either an aptamer as described herein or an aptamer conjugate as described herein to the subject. In specific embodiments, administering an aptamer or aptamer conjugate comprises administering a pharmaceutical formulation comprising the aptamer or aptamer conjugate.

Some embodiments relate to a method of treating cancer in a human subject, comprising administering an effective amount of either an aptamer as described herein or an aptamer conjugate as described herein to the subject. In specific embodiments, administering an aptamer or aptamer conjugate comprises administering a pharmaceutical formulation comprising the aptamer or aptamer conjugate.

Some embodiments relate to a method of administering an aptamer to a human subject, comprising administering either an aptamer as described herein or an aptamer conjugate as described herein to the subject. In specific embodiments, administering an aptamer or aptamer conjugate comprises administering a pharmaceutical formulation comprising the aptamer or aptamer conjugate.

Some embodiments relate to a method of treating cancer in a human subject, comprising administering an effective amount of an aptamer or aptamer conjugate to the subject, wherein the cancer comprises cancer cells that express MISIIR, and the aptamer or aptamer conjugate specifically binds MISIIR. In specific embodiments, the aptamer or aptamer conjugate comprises a nucleotide sequence that varies from the nucleotide sequences disclosed herein. In specific embodiments, administering an aptamer or aptamer conjugate comprises administering a pharmaceutical formulation comprising the aptamer or aptamer conjugate.

Some embodiments relate to a method of transporting a pharmaceutical agent across a cell membrane of a cancer cell in a human subject, comprising administering an aptamer conjugate as described herein to the subject, wherein the aptamer conjugate comprises the pharmaceutical agent. In specific embodiments, administering an aptamer or aptamer conjugate comprises administering a pharmaceutical formulation comprising the aptamer or aptamer conjugate.

Some embodiments relate to a method of killing a cancer cell in a human subject, comprising administering an aptamer conjugate as described herein to the subject, wherein the aptamer conjugate comprises a pharmaceutical agent. In specific embodiments, administering an aptamer or aptamer conjugate comprises administering a pharmaceutical formulation comprising the aptamer or aptamer conjugate. In some embodiments, the cancer cell is a metastatic cancer cell.

In some embodiments, a subject is selected from murines, lagomorpha, felines, canines, porcines, ovines, bovines, equines, and primates. In specific embodiments, the subject is human.

In some embodiments, a subject is female. In specific embodiments, the subject is a human female. In more specific embodiments, the subject is a human female who presents with cancer. In very specific embodiments, the subject is a human female who presents with ovarian cancer or breast cancer.

In some embodiments, a subject is male. In specific embodiments, the subject is a human male. In more specific embodiments, the subject is a human male who presents with cancer. In very specific embodiments, the subject is a human male who presents with prostate cancer.

In some embodiments, a subject has cancer. In specific embodiments, at least some cancer cells of the cancer express MISIIR. In specific embodiments, the cancer is ovarian cancer, breast cancer, or prostate cancer. In more specific embodiments, the cancer is epithelial ovarian cancer, ovarian dysgerminoma, endometrial cancer, uterine malignant mixed Müllerian tumor, uterine leiomyosarcoma, or endometrial stromal sarcoma. In more specific embodiments, the cancer is ovarian endometrioid adenocarcinoma, ovarian serous adenocarcinoma, epithelial ovarian carcinoma, germ cell cancer, stromal cell cancer, primary peritoneal cancer, or fallopian tube carcinoma. In very specific embodiments, the cancer is ovarian endometrioid adenocarcinoma, ovarian serous adenocarcinoma, or malignant epithelial ovarian carcinoma.

In some embodiments, a subject has cancer, and the cancer is metastatic cancer. In specific embodiments, the subject has metastatic cancer cells that express MISIIR.

In some embodiments, a subject comprises a mutant BRCA1 gene, the subject has cancer, and the mutant BRCA1 gene is associated with the cancer.

In some embodiments, a subject comprises a mutant BRCA2 gene, the subject has cancer, and the mutant BRCA2 gene is associated with the cancer.

In some embodiments, a subject is a human female who previously received a fertility drug. In specific embodiments, the fertility drug is menotropin or follicle stimulating hormone.

In some embodiments, a subject is a human female who has never been pregnant.

In some embodiments, a subject has previously undergone surgery to remove or ablate all or part of a tumor, uterus, cervix, ovary, fallopian tube, or prostate. In specific embodiments, the subject previously underwent a hysterectomy, oophorectomy, or prostatectomy.

In some embodiments, a subject is a human who has cancer, and the method increases the predicted survival of the subject. In specific embodiments, the method increases the predicted survival of the subject by at least 6, 12, or 24 months. In very specific embodiments, the method increases the predicted survival of the subject by at least 6 months.

In some embodiments, a subject is a human who has cancer, and the method increases the predicted chance of 5-year survival of the subject. In specific embodiments, the method increases the predicted survival of the subject from less than 50% to greater than 50%.

In some embodiments, administering an aptamer or aptamer conjugate comprises administering a pharmaceutical formulation comprising the aptamer or aptamer conjugate. In specific embodiments, the pharmaceutical formulation is a liquid or liquid suspension. In more specific embodiments, the pharmaceutical formulation is an aqueous liquid or an aqueous liquid suspension. In specific embodiments, the pharmaceutical formulation is an aqueous liquid or an aqueous liquid suspension, and the pharmaceutical formulation is approximately isotonic with human blood. In specific embodiments, the pharmaceutical formulation is an aqueous liquid or an aqueous liquid suspension, and the pharmaceutical formulation has a pH of about 7.0 to about 8.0. In more specific embodiments, the pharmaceutical formulation comprises a pH buffer. In very specific embodiments, the pH buffer comprises a Brønsted acid having a pKa between about 7.0 and about 8.0. Appropriate pharmaceutical formulations are known and published, for example, in REMINGTON: THE SCIENCE AND PRACTICE OF PHARMACY (Loyd V. Allen Jr. ed., 22d ed. 2013).

In some embodiments, administering comprises injecting. In specific embodiments, administering comprises intravenous injection, subcutaneous injection, intramuscular injection, intratumoral injection, peritumoral injection, or intraperitoneal injection.

In some embodiments, a method further comprises administering a second pharmaceutical agent to the subject. In specific embodiments, the second pharmaceutical agent is a chemotherapeutic agent. In more specific embodiments, the second pharmaceutical agent is a platinum-based therapy, alkylating agent, taxane, or folate receptor-targeting agent. In very specific embodiments, the second pharmaceutical agent is cisplatin, carboplatin, cis-diamminedichloro platinum (II), cyclophosphamide, paclitaxel, or doxetaxel. In very specific embodiments, the second pharmaceutical agent is ONX-0801, vintafolide, or farletuzumab.

EXEMPLIFICATION

Example 1. Identification of Aptamers that Specifically Bind MISIIR

Figure 5:
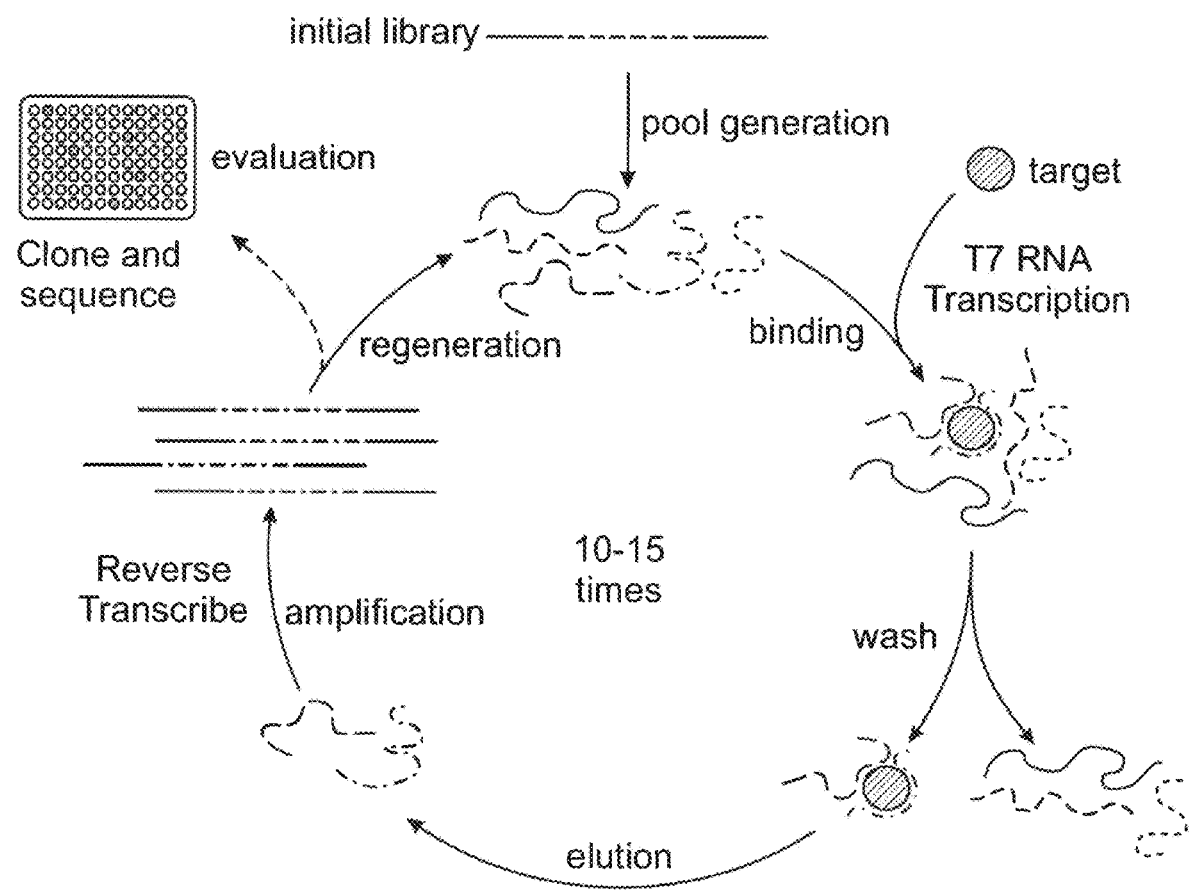
FIG. 5 is a cartoon that depicts methods used to identify the aptamer nucleotide sequences disclosed herein.

Aptamers that specifically bind MISIIR were generated from an initial library by (1) generating a pool of DNA encoding aptamer variants, (2) transcribing the pools of DNA into RNA aptamers, (3) incubating the aptamers with the MISIIR extracellular domain, (4) isolating the MISIIR extracellular domain and aptamers bound thereto from unbound aptamers, (5) reverse transcribing the bound aptamers into DNA, (6) introducing mutations into the DNA, thereby generating a new pool of DNA encoding aptamer variants, and (7) iteratively repeating the foregoing steps (FIG. 5). After 9 iterations, DNA encoding the aptamer variants was cloned and sequenced. DNA nucleotide sequences encoding various aptamers identified using the foregoing strategy are disclosed in SEQ ID NO:9 to SEQ ID NO:77. These DNA nucleotide sequences correspond to RNA aptamers (and not their reverse complements). SEQ ID NO:77 displays a disparate sequence and lower binding affinity than the aptamers of SEQ ID NO:9 to SEQ ID NO:76, and SEQ ID NO:77 was used as a control in subsequent experiments.

Example 2. Determination of Aptamer Dissociation Constants

The dissociation constants of four different aptamers were determined under a variety of conditions. "Aptamer 1" as the term is utilized herein refers to an aptamer consisting of the nucleotide sequence set forth in SEQ ID NO:1. "Aptamer 2" as the term is utilized herein refers to an aptamer consisting of the nucleotide sequence set forth in SEQ ID NO:5. "Aptamer 3" as the term is utilized herein refers to an aptamer consisting of the nucleotide sequence set forth in SEQ ID NO:7. "Aptamer 8" as the term is utilized herein refers to an aptamer consisting of the nucleotide sequence set forth in SEQ ID NO:77, and Aptamer 8 was used as a control aptamer.

Figure 6:
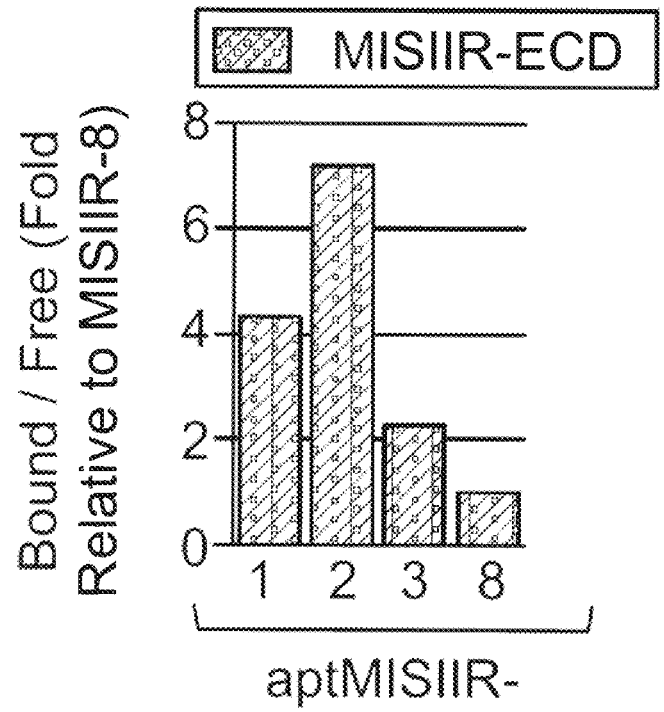
FIG. 6 is a graph depicting the relative binding of four different aptamers to the Müllerian inhibitory substance II receptor (MISIIR) extracellular domain. Aptamers 1, 2, 3, and 8, have the nucleotides sequences set forth in SEQ ID NO: 1, 5, 7, and 77, respectively. Aptamers 1, 2, and 3 display higher binding affinity to the MISIIR extracellular domain than Aptamer 8.

Relative binding affinities and dissociation constants were determined for Aptamers 1, 2, 3, and 8 by (1) incubating $\gamma$-$^{32}$P-labelled aptamer with beads coated with the MISIIR extracellular domain at a 10 nM concentration, (2) washing the beads to remove unbound aptamer, (3) measuring the concentration of bound aptamer using a scintillation counter, and (4) calculating the dissociation constants using non-linear curve regression. Aptamer 1 and Aptamer 2 displayed higher binding affinity and lower dissociation constants than Aptamer 3 and Aptamer 8 (FIG. 6). The dissociation constant of Aptamer 1 was determined to be 1.8±1 nM. The dissociation constant of Aptamer 2 was determined to be 1.5±0.5 nM.

Relative binding affinities were determined for Aptamers 1, 2, 3, and 8 by (1) incubating $\gamma$-$^{32}$P-labelled aptamer with 100,000 of either IGROV-1 cells, OVCA433 cells, or OVCAR8 cells for 30 minutes at 37° C., (2) separating the cells and aptamer bound thereto from unbound aptamer, (3) measuring the concentration of bound aptamer using a scintillation counter, and (4) calculating the dissociation constants using non-linear curve regression. IGROV-1 cells are human ovarian endometrioid adenocarcinoma cells.

OVCA433 are human ovarian serous adenocarcinoma cells. OVCAR-8 cells are human high grade ovarian serous adenocarcinoma cells.

Figure 7:
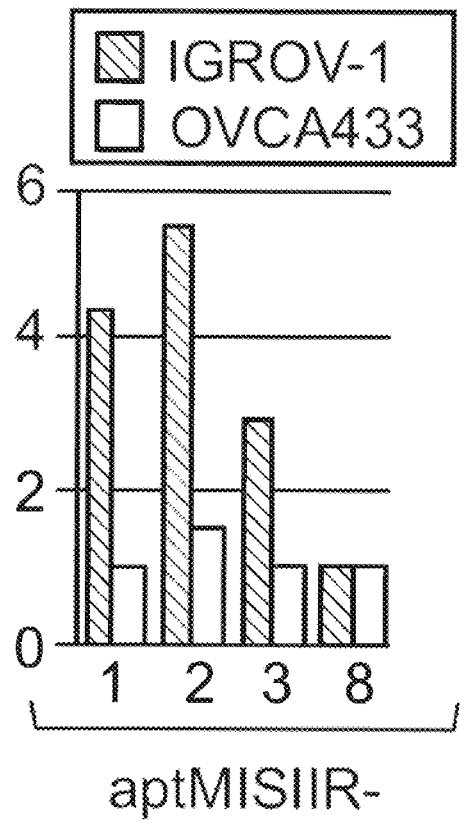
FIG. 7 is a graph depicting the relative binding affinity of four different aptamers to IGROV-1 cells, which are ovarian endometrioid adenocarcinoma cells, and OVCA433 cells, which are ovarian serous adenocarcinoma cells. Aptamers 1, 2, and 3 display higher binding affinity to IGROV-1 cells than Aptamer 8. Aptamer 2 displays higher binding affinity to OVCA433 cells than Aptamers 1, 3, and 8.

Aptamer 1 and Aptamer 2 displayed higher binding affinity and lower dissociation constants than Aptamer 3 and Aptamer 8 relative to IGROV-1 cells (FIG. 7) and OVCAR-8 cells (data not shown). Aptamer 2 displayed a higher binding affinity and a lower dissociation constant than Aptamer 1, Aptamer 3, and Aptamer 8 relative to OVCA433 cells (FIG. 7).

Example 3. Aptamer 1 and Aptamer 2 Bind Cancer Cells that Express MISIIR and Induce Endocytosis OVCAR-8 cells were incubated for 1 hour at 37° C. with fluorescently-labeled Aptamer 1, Aptamer 2, or Aptamer 8, which was used as a control. Cells were then washed, incubated in fresh media for 3 hours, fixed with formaldehyde, and stained with the nuclear stain 4',6-diamidino-2-phenylindole (DAPI). Aptamer 1 and Aptamer 2 both bound OVCAR-8 cells as determined by confocal microscopy (FIG. 8, left column, top and middle rows, respectively). Aptamer 8 did not display appreciable binding to OVCAR-8 cells (FIG. 8, left column, bottom row).

Figure 8:
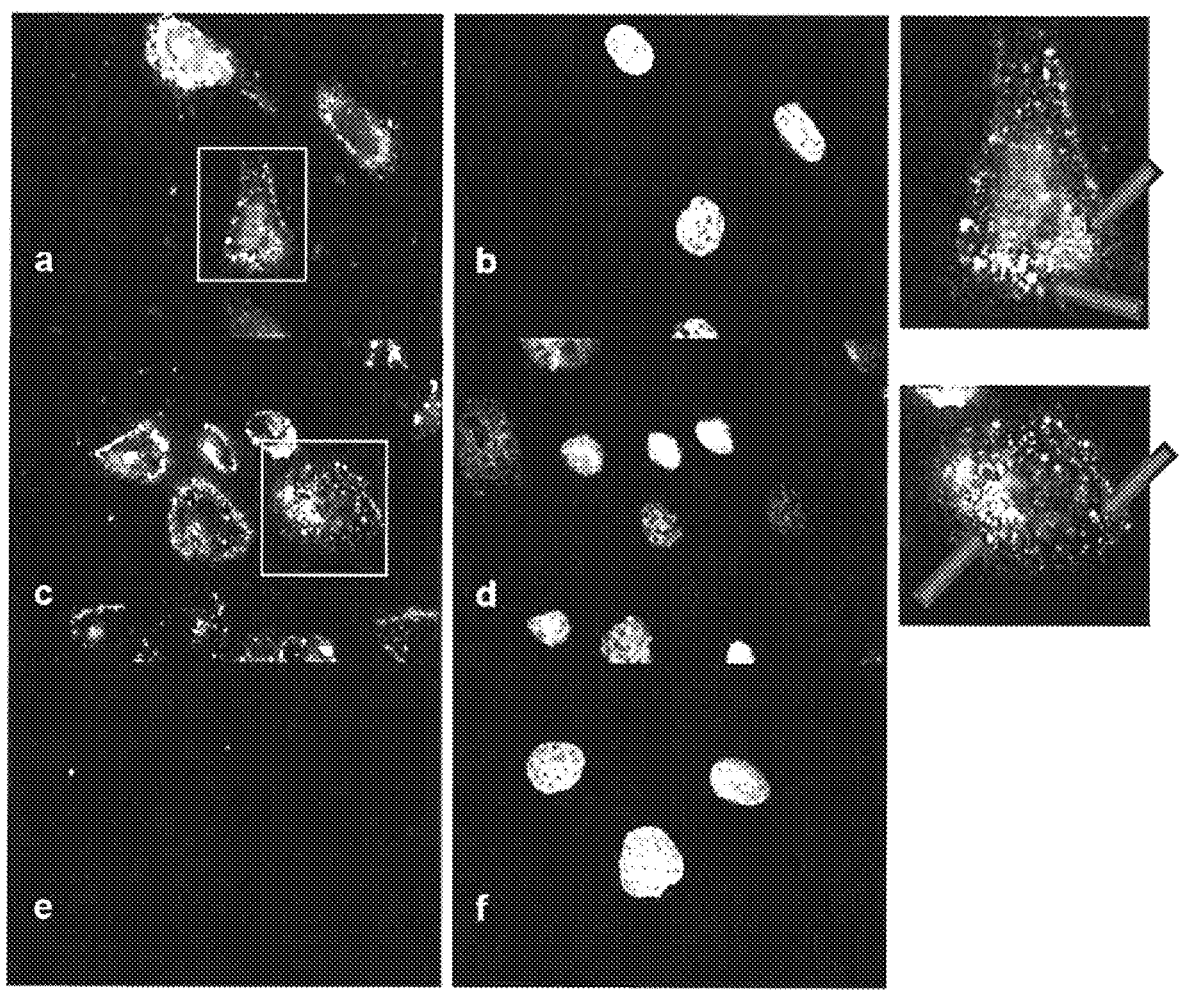
FIG. 8 depicts confocal microscopy images of OVCAR-8 cells that were contacted with different fluorescently-labelled aptamers. The top row depicts cells that were contacted with fluorescently-labelled Aptamer 1, which has the nucleotide sequence set forth in SEQ ID NO:1. The middle row depicts cells that were contacted with fluorescently-labelled Aptamer 2, which has the nucleotide sequence set forth in SEQ ID NO:5. The bottom row depicts cells that were contacted with a fluorescently-labelled control aptamer, Aptamer 8, which has the nucleotide sequence set forth in SEQ ID NO:77. The left column depicts aptamer-associated fluorescence. The middle column depicts fluorescence corresponding to the nuclear stain DAPI. The right column depicts images of the cells demarcated by squares in the left column; arrows denote speckled fluorescence indicative of intracellular vesicles.

Confocal microscopy images of OVCAR-8 cells incubated with either Aptamer 1 or Aptamer 2 revealed speckled fluorescence patterning consistent with intracellular vesicles, which suggests that Aptamer 1 and Aptamer 2 entered OVCAR-8 cells by endocytosis (FIG. 8, right column, top and middle rows, respectively). Diffuse staining within the cytoplasm indicated that Aptamer 1 and Aptamer 2 were also released into the cytosol (FIG. 8, right column, top and middle rows, respectively). Aptamer 8, which was used as a control, did not display speckled fluorescence patterning or diffuse staining within the cytoplasm.

Example 4. Aptamer 1 Localizes to Ovarian Cancer Cells In Vivo and Likely Enters the Cancer Cells The tail vein of three SCID mice comprising OVCAR-8 cell tumors was injected with vehicle or 10 μg of fluorescently-labeled aptamer-miRNA conjugate comprising a 24-residue nucleotide sequence derived from either Aptamer 1 or Aptamer 8 (control). The mice were imaged at 2, 24, 48, and 72 hours using a Xenogen IVIS Spectrum imager (FIG. 9).

Figure 9:
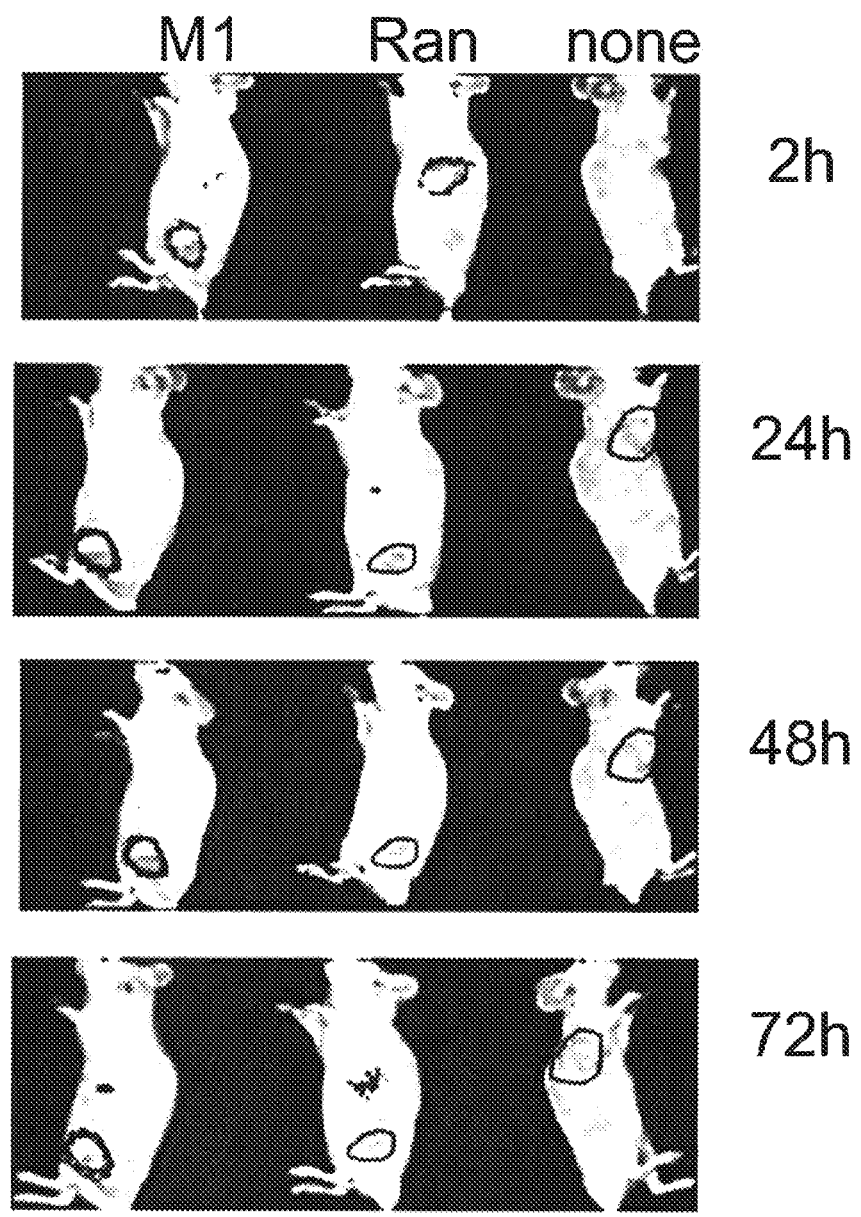
FIG. 9 depicts fluorescence images of three mice that have OVCAR-8 cell tumors and that were injected with either an aptamer conjugate comprising a 24-residue nucleotide sequence derived from Aptamer 1, miRNA, and fluorophore cyanine 5 ("Cy5"); a similarly-conjugated control aptamer conjugate comprising a 24-residue nucleotide sequence derived from Aptamer 8; or vehicle. The aptamer conjugate derived from Aptamer 1 localized to the OVCAR-8 tumor whereas the control aptamer conjugate did not.
Figure 10:
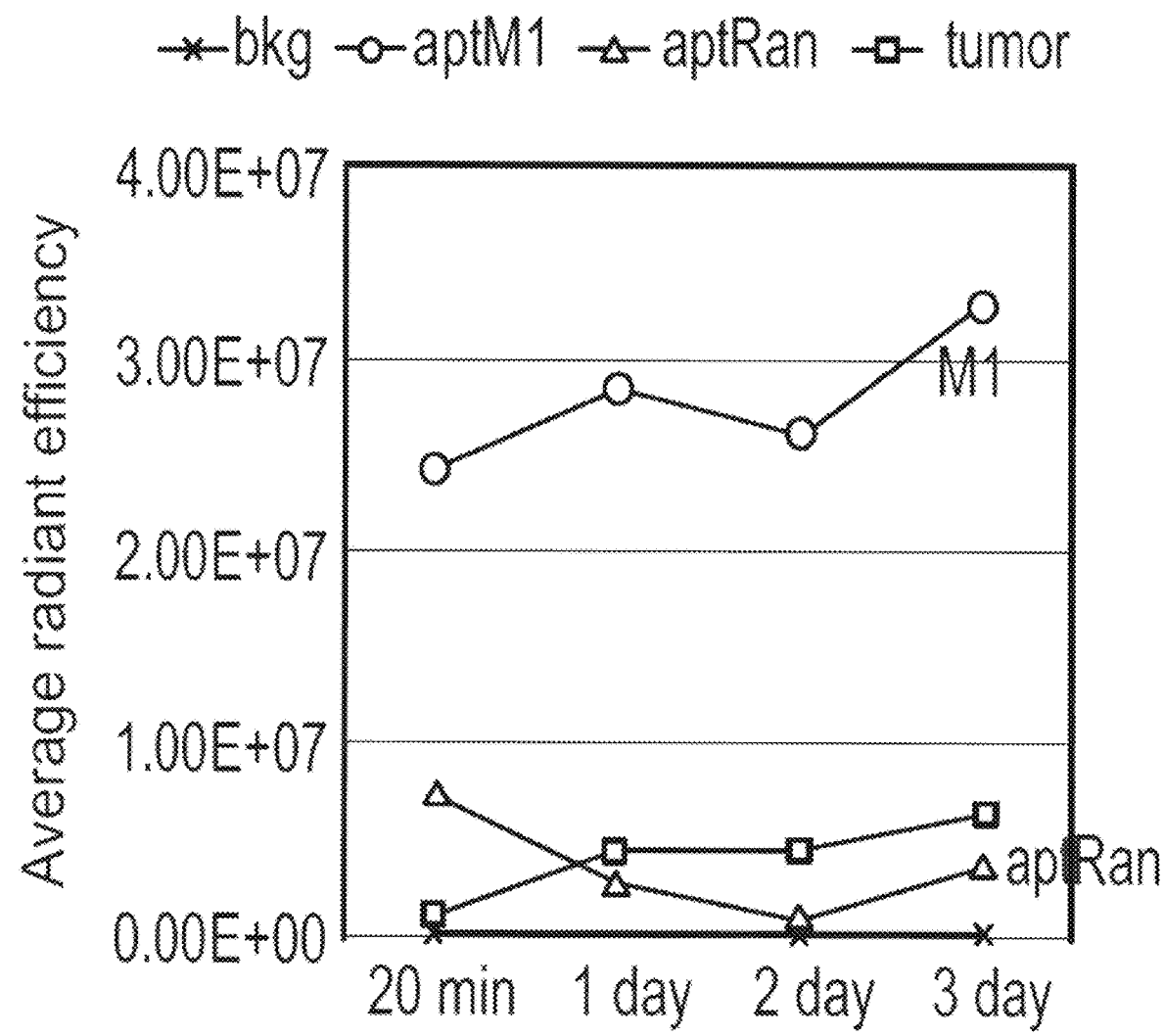
FIG. 10 is a graph that depicts average radiant efficiency at the site of an OVCAR-8 tumor in mice after injection with an aptamer conjugate derived from Aptamer 1 ("M1"; ---⊖--- ) or a control aptamer conjugate derived from Aptamer 8 ("aptRan"; ---▲--- ). Other datapoints correspond to background ("bkg"; ---✶--- ) and tumor ( ---⊞--- ). The aptamer conjugate derived from Aptamer 1 displayed higher radiant efficiency than the control aptamer conjugate.

The mouse injected with the fluorescently-labeled aptamer conjugate derived from Aptamer 1 displayed strong fluorescence intensity in the region of the OVCAR-8 cell tumor at 2 hours, and this fluorescence persisted through 72 hours (FIG. 9, left column; FIG. 10, "M1" & ). This result suggests that the aptamer conjugate specifically bound OVCAR-8 cancer cells and crossed the cell membrane thereby sequestering the fluorescent label intracellularly within the cancer cells.

The mouse injected with the fluorescently-labeled aptamer conjugate derived from Aptamer 8 displayed fluorescence indicative of rapid clearance of the aptamer conjugate and only nominal fluorescence at timepoints beyond 2 hours (FIG. 9, middle column; FIG. 10, "aptRan" & ).

Mice were sacrificed at 72 hours. Fluorescence was observed ex vive in tumors from the mouse treated with the aptamer conjugate derived from Aptamer 1. The ovary, heart, liver, spleen, and kidney were examined histologically to detect any changes in cell morphology and necrosis using Hemoxylin & Eosin staining. No evidence of toxicity was observed.

Example 5. Aptamer 1 and Aptamer 2 Localize to Ovarian Cancer Cells In Vivo and Likely Enter the Cancer Cells The tail vein of four SCID mice comprising IGROV-1 cell tumors was injected with vehicle or 10 μg of fluorescently-labeled aptamer-miRNA conjugate comprising a 24-residue nucleotide sequence derived from either Aptamer 1, Aptamer 2, or Aptamer 8 (control). The mice were imaged at 2, 24, 48, and 72 hours using a Xenogen IVIS Spectrum imager (FIG. 11).

Figure 11:
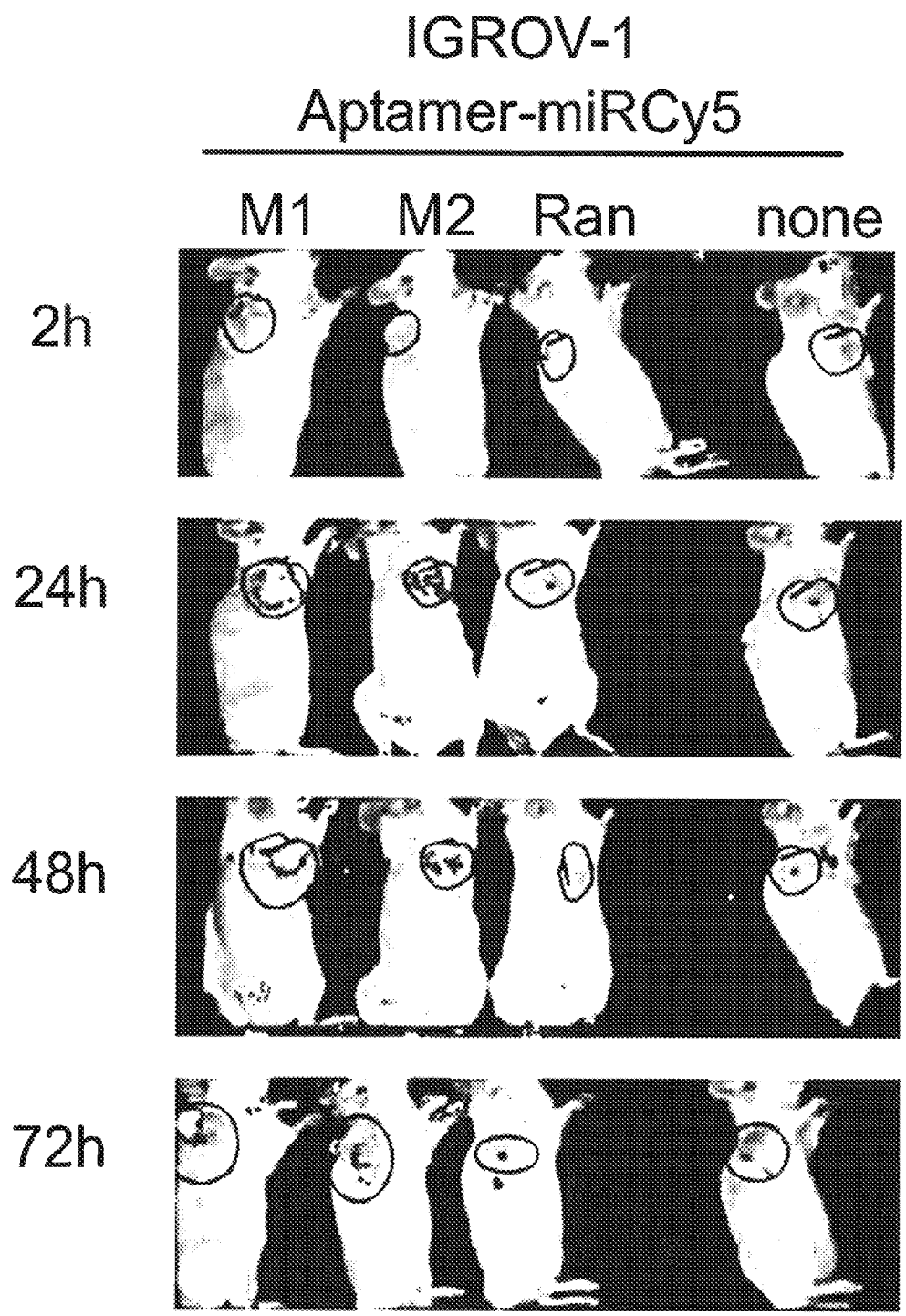
FIG. 11 depicts fluorescence images of three mice that have IGROV-1 cell tumors and that were injected with either an aptamer conjugate comprising a 24-residue nucleotide sequence derived from Aptamer 1, miRNA, and fluorophore cyanine 5 ("Cy5"); a similarly-conjugated aptamer conjugate comprising a 24-residue nucleotide sequence derived from Aptamer 2; a similarly-conjugated control aptamer conjugate comprising a 24-residue nucleotide sequence derived from Aptamer 8; or vehicle. The aptamer conjugates derived from Aptamers 1 and 2 localized to the IGROV-1 tumor whereas the control aptamer conjugate did not.
Figure 12:
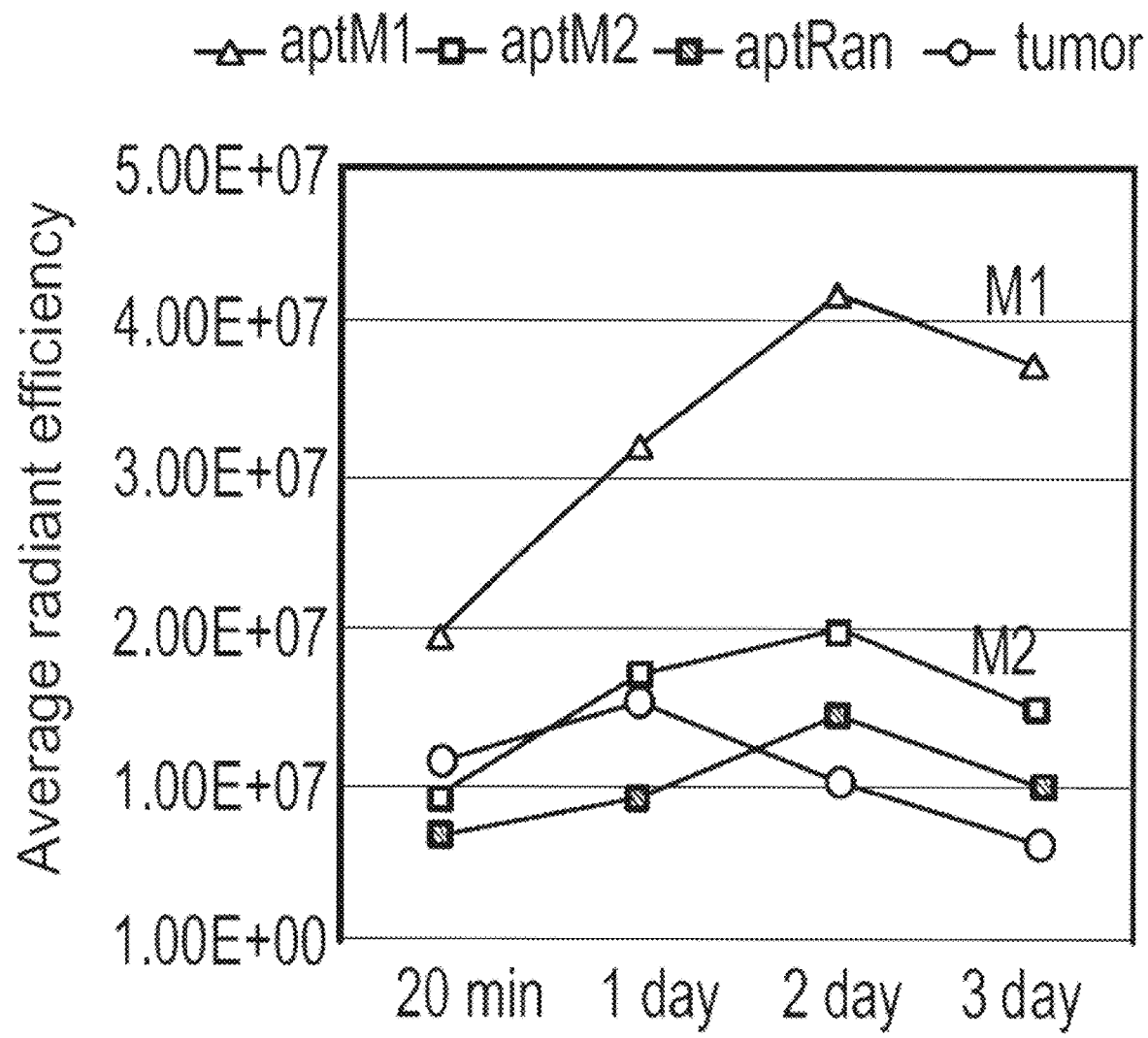
FIG. 12 is a graph that depicts average radiant efficiency at the site of an IGROV-1 tumor in mice after injection with an aptamer conjugate derived from Aptamer 1 ("M1"; -▲-), an aptamer conjugate derived from Aptamer 2 ("M2"; -□-), or a control aptamer conjugate derived from Aptamer 8 ("aptRan"; -▒-). Other datapoints correspond to tumor (-◇-). The aptamer conjugate derived from Aptamer 1 displayed higher radiant efficiency than the control aptamer conjugate. The aptamer conjugate derived from Aptamer 2 displayed higher radiant efficiency than the control aptamer conjugate at timepoints greater than 2 hours.

The mouse injected with the fluorescently-labeled aptamer conjugate derived from Aptamer 1 displayed strong fluorescence intensity in the region of the IGROV-1 cell tumor at 2 hours, and this fluorescence persisted through 72 hours (FIG. 11, left column; FIG. 12, "M1" & ). This result suggests that the aptamer conjugate specifically bound IGROV-1 cancer cells and crossed the cell membrane thereby sequestering the fluorescent label intracellularly within the cancer cells.

The mouse injected with the fluorescently-labeled aptamer conjugate derived from Aptamer 2 displayed strong fluorescence intensity in the region of the IGROV-1 cell tumor at 2 hours, and this fluorescence persisted through 72 hours (FIG. 11, second column from left; FIG. 12, "M2"& ). This result suggests that the aptamer conjugate specifically bound IGROV-1 cancer cells and crossed the cell membrane thereby sequestering the fluorescent label intracellularly within the cancer cells.

The mouse injected with the fluorescently-labeled aptamer conjugate derived from Aptamer 8 displayed fluorescence indicative of rapid clearance of the aptamer conjugate and only nominal fluorescence at timepoints beyond 2 hours (FIG. 11, third column from left; FIG. 12, "aptRan" & ).

Mice were sacrificed at 72 hours. Fluorescence was observed ex vivo in tumors from the mouse treated with the aptamer conjugates derived from Aptamer 1 and Aptamer 2. The ovary, heart, liver, spleen, and kidney were examined histologically to detect any changes in cell morphology and necrosis using Hemoxylin & Eosin staining. No evidence of toxicity was observed.

Those skilled in the art will recognize, or be able to ascertain using no more than routine experimentation, many equivalents to the specific embodiments of the invention described herein. The scope of the present invention is not intended to be limited to the above Description and Examples, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given composition or method. The invention also includes embodiments in which more than one, or all group members are present in, employed in, or otherwise relevant to a given composition or method. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. It should also be understood that, in general, where the invention, or embodiments and aspects of the invention, is/are referred to as comprising particular elements, features, etc., certain embodiments of the invention or aspects of the invention consist, or consist essentially of, such elements, features, etc. "Consist essentially" in accordance with the disclosure means that in addition to the recited element(s), non-essential elements may or may not be present.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein.

What is claimed is:

1. An aptamer, comprising a nucleotide sequence having at least 95% sequence homology with at least 24 consecutive nucleotides of the nucleotide sequence set forth in SEQ ID NO:4.

2. The aptamer of claim 1, wherein the aptamer comprises one or more halogenated nucleotides or one or more 2'-substituted nucleotides.

3. The aptamer of claim 2, wherein the aptamer comprises a 2'-fluoropyrimidine.

4. The aptamer of claim 1, comprising 100% nucleobase sequence identity with at least 24 consecutive nucleotides of the nucleotide sequence set forth in SEQ ID NO:4.

5. The aptamer of claim 1, comprising the nucleotide sequences set forth in SEQ ID NO:2 and SEQ ID NO:3, or 2'-fluoropyrimidine-substituted variant(s) thereof, wherein the nucleotides of SEQ ID NO:2 and SEQ ID NO:3, or the nucleotides of the 2'-fluoropyrimidine-substituted variant(s) thereof, form an intramolecular double strand comprising wobble base pairs.

6. The aptamer of claim 1, comprising the secondary structure set forth in either Compound I or Compound II.

7. The aptamer of claim 1, wherein the aptamer specifically binds Müllerian inhibitory substance II receptor (MISIIR) with a dissociation constant less than 1 µM.

8. The aptamer of claim 1, wherein the aptamer specifically binds to cells expressing Müllerian inhibitory substance II receptor (MISIIR), and the aptamer does not specifically bind to cells that lack MISIIR.

9. The aptamer of claim 8, wherein the aptamer is capable on inducing endocytosis upon binding a cell that expresses MISIIR.

10. An aptamer conjugate, comprising the aptamer of claim 1.

11. The aptamer conjugate of claim 10, wherein:
the aptamer conjugate comprises a pharmaceutical agent;
the aptamer conjugate is an aptamer-drug conjugate; and
the pharmaceutical agent of the aptamer-drug conjugate is a siRNA, a microRNA, a chemotherapeutic, a photosensitizer, a photothermal agent, an immunotherapeutic, a radiopharmaceutical agent, or an enzyme.

12. A nucleic acid, comprising a DNA nucleotide sequence encoding the aptamer of claim 1.

13. The nucleic acid of claim 12, wherein the DNA nucleotide sequence is operably-linked to a promoter.

14. An isolated comprising the nucleic acid of claim 12.

15. An aptamer, comprising a nucleotide sequence having at least 95% sequence homology with nucleotides 33 to 73 of the nucleotide sequence set forth in any one of SEQ ID NO:9-76.

16. A method of treating a human subject suffering from cancer, comprising administering an aptamer to the subject, wherein the aptamer comprises a RNA nucleotide sequence having at least 95% sequence homology with at least 24 consecutive nucleotides of the nucleotide sequence set forth in SEQ ID NO:4.

17. The method of claim 16, wherein the subject has ovarian cancer, breast cancer, or prostate cancer.

18. The method of claim 17, wherein the subject has ovarian endometrioid adenocarcinoma, ovarian serous adenocarcinoma, or malignant epithelial ovarian carcinoma.

19. The method of claim 16, wherein cells of the cancer express Müllerian inhibitory substance II receptor (MISIIR).

* * * * *